United States Patent [19]

Shadle et al.

[11] Patent Number: 5,153,265
[45] Date of Patent: Oct. 6, 1992

[54] CONJUGATION OF POLYMER TO COLONY STIMULATING FACTOR-1

[75] Inventors: Paula J. Shadle, Belmont; Kirston E. Koths, El Cerrito; Margaret Moreland, Berkeley; Nandini Katre, El Cerrito; Walter J. Laird, Pinole; Lois Aldwin, San Mateo; Danute E. Nitecki, Berkeley; John D. Young, Walnut Creek, all of Calif.

[73] Assignee: Cetus Corporation, Emeryville, Calif.

[21] Appl. No.: 576,415

[22] PCT Filed: Jan. 23, 1989

[86] PCT No.: PCT/US89/00270

§ 371 Date: Aug. 30, 1990

§ 102(e) Date: Aug. 30, 1990

Related U.S. Application Data

[63] Continuation-in-part of Ser. No. 146,275, Jan. 20, 1988, Pat. No. 4,847,325.

[51] Int. Cl.$^5$ .................. C08L 89/00; C07G 7/00; A61K 37/02
[52] U.S. Cl. .................. 525/54.1; 530/351; 530/410; 530/413; 514/12
[58] Field of Search ........... 530/351, 410, 413; 525/54.1; 435/68; 514/2, 12; 424/85.1

[56] References Cited

U.S. PATENT DOCUMENTS 4,094,744  6/1978  Hartdegen et al. ........... 525/54.1
4,847,325  7/1989  Shadle et al. ................ 530/351

Primary Examiner—Nathan M. Nutter
Attorney, Agent, or Firm—Philip L. McGarrigle; Jane R. McLaughlin; Albert P. Halluin

[57] ABSTRACT

A biologically active CSF-1 protein is selectively conjugated via certain amino acid residues or carbohydrate moieties to a water-soluble polymer selected from polyethylene glycol or polypropylene glycol homopolymers, polyoxyethylated polyols, or polyvinyl alcohol. The resulting conjugated CSF-1 is biologically active and has increased circulating half-life in mammals, compared to that of the unconjugated protein. The conjugated CSF-1 may be used to stimulate the immune response or to provide more cells to be stimulated.

33 Claims, 9 Drawing Sheets

```
                    20                        40                        60
AGTGAGGCTC  GGCCCGGGGA  AAGTGAAAGT  TTGCCTGGGT  CCTCTCCGGCG  CCAGAGCCGC 80                       100                       120
TCTCCGCATC  CCAGGACAGC  GGTGCGGCCC  TCGGCCGGGG  CGCCCACTCC  GCAGCAGCCA
                                                      ▲
                   140                       160                       180
GCGAGCGAGC  GAGCGAGCGA  GGGCGGCCGA  CGCGCCCGGC  CGGGACCCAG  CTGCCCGT ATG
                                                                     Met
                                                                     -32
                    200                                    220
ACC GCG CCG GGC GCC GCC GGG CGC TGC CCT CCC ACG ACA TGG CTG GGC
Thr Ala Pro Gly Ala Ala Gly Arg Cys Pro Pro Thr Thr Trp Leu Gly 240                          260                       280
TCC CTG CTG TTG TTG GTC TGT CTC CTG GCG AGC AGG AGT ATC ACC GAG GAG
Ser Leu Leu Leu Leu Val Cys Leu Leu Ala Ser Arg Ser Ile Thr Glu Glu
                                                             1━━━━━━━

300                          320
GTG TCG GAG TAC TGT AGC CAC ATG ATT GGG AGT GGA CAC CTG CAG TCT
Val Ser Glu Tyr Cys Ser His Met Ile Gly Ser Gly His Leu Gln Ser 340                       360                       380
CTG CAG CGG CTG ATT GAC AGT CAG ATG GAG ACC TCG TGC CAA ATT ACA TTT GAG
Leu Gln Arg Leu Ile Asp Ser Gln Met Glu Thr Ser Cys Gln Ile Thr Phe Glu
         20  INTRON ↑ SEQUENCE 400                           420
TTT GTA GAC CAG GAA CAG TTG AAA GAT CCA GTG TGC TAC CTT AAG
Phe Val Asp Gln Glu Gln Leu Lys Asp Pro Val Cys Tyr Leu Lys
             40

440                           460                       480
AAG GCA TTT CTC CTG GTA CAA TAC ATA ATG GAG GAC ACC ATG CGC TTC AGA GAT
Lys Ala Phe Leu Leu Val Gln Tyr Ile Met Glu Asp Thr Met Arg Phe Arg Asp
                                  * 60

500                           520
AAC ACC CCC AAT GCC ATC GCC ATT GTG CAG CTG CAG GAA CTC TCT
Asn Thr Pro Asn Ala Ile Ala Ile Val Gln Leu Gln Glu Leu Ser
                                         80

540                            560
TTG AGG CTG AAG AGC TGC TTC ACC AAG GAT TAT GAA GAG CAT GAC AAG GCC
Leu Arg Leu Lys Ser Cys Phe Thr Lys Asp Tyr Glu Glu His Asp Lys Ala
                                                                100
580                             600                          620
TGC GTC CGA ACT TTC TAT GAG ACA CCT CTC CAG TTG CTG GAG AAG GTC
Cys Val Arg Thr Phe Tyr Glu Thr Pro Leu Gln Leu Leu Glu Lys Val 640                           660
AAG AAT GTC TTT AAT GAA ACA AAG AAT CTC CTT GAC AAG GAC TGG AAT ATT
Lys Asn Val Phe Asn Glu Thr Lys Asn Leu Leu Asp Lys Asp Trp Asn Ile
              120        ━━━━━━━━━━━━━━━━━━━━━━━━━━━━━━━━━━━━━━━━━━
```

FIG. 1-1

```
                680                      700                         720
        TTC AGC AAG AAC TGC AAC AAC AGC TTT GCT GAA TGC TCC AGC CAA GGC
        Phe Ser Lys Asn Cys Asn Asn Ser Phe Ala Glu Cys Ser Ser Gln Gly
                                140
                    740                         760
        CAT GAG AGG CAG TCC GAG GGA TCC TCC AGC CCG CAG CTC CAG GAG TCT GTC
        His Glu Arg Gln Ser Glu Gly Ser Ser Ser Pro Gln Leu Gln Glu Ser Val
                                       160
                780                         800                    820
        TTC CAC CTG CTG GTG CCC AGT GTC ATC CTG GTC TTG CTG GCC GTG GGA
        Phe His Leu Leu Val Pro Ser Val Ile Leu Val Leu Leu Ala Val Gly
                                                         180
                        840                         860
        GGC CTC TTG TTC TAC AGG TGG AGG CGG CGG AGC CAT CAA GAG CCT CAG AGA
        Gly Leu Leu Phe Tyr Arg Trp Arg Arg Arg Ser His Gln Glu Pro Gln Arg
                                                                       200
                880                         900                      920
        GCG GAT TCT CCC TTG GAG CAA CCA GAG GGC AGC CCC CTG ACT CAG GAT
        Ala Asp Ser Pro Leu Glu Gln Pro Glu Gly Ser Pro Leu Thr Gln Asp
                        940                         960                       980
        GAC AGA CAG GTG GAA CTG CCA GTG TAG AGGGAATTCTA AGACCCCTCA CCATCCTGGA
        Asp Arg Gln Val Glu Leu Pro Val
                        220
                       1000                    1020
        CACACTCGTT TGTCAATGTC CCTCTGAAAA TGTGACGCCC AGCCCCGGAC
                       1040                    1060                     1080                    1100
        ACAGTACTCC AGATGTTGTC TGACCAGCTC AGAGAGAGTA CAGTGGGACT GTTACCTTCC TTGATATGGA
                       1120                    1140
        CAGTATTCTT CTATTTGTGC AGATTAAGAT TGCATTAGTT TTTTTCTTAA
                       1160                    1180                    1200                      1220
        CAACTGCATC ATACTGTTGT CATATGTTGA GCCTGTGGTC TATTAAAACC CCTAGTTCCA TTTCCCATAA
                                                                                                  ▲
                       1240                    1260
        ACTTCTGTCA AGCCAGACCA TCTCTACCCT GTACTTGGAC AACTTAACTT
                       1280                    1300                    1320                      1340
        TTTTAACCAA AGTGCAGTTT ATGTTCACCT TTGTTAAAGC CACCTTGTGG TTTCTGCCCA TCACCTGAAC
                       1360                    1380
        CTACTGAAGT TGTGTGAAAT CCTAATTCTG TCATCTCCGT AGCCCTCCCA
                       1400                    1420                    1440                      1460
        GTTGTGCCTC CTGCACATTG ATGAGTGCCT GCTGTTGTCT TTGCCCATGT TGTTGATGTA GCTGTGACCC
                       1480                    1500
        TATTGTTCCT CACCCCTGCC CCCGCCAAC CCCAGCTGGC CCACCTCTTC
                       1520                    1540                    1560                      1580
        CCCCTCCCAC CCAAGCCCAC AGCCAGCCCA TCAGGAAGCC TTCCTGGCTT CTCCACAACC TTCTGACTGC
                       1600                    1620
        TCTTTTCAGT CATGCCCCTC CTGCTCTTTT GTATTTGGCT AATAGTATAT
                       1640
        CAATTTGCAC TT
```

FIG. 1-2

```
                CCCTGCTGTTGTTGGTCTGTCTCCTGGCGAGCAGGAGTATCACC   44
            -14 LeuLeuLeuLeuValCysLeuLeuAlaSerArgSerIleThr

GAGGAGGTGTCGGAGTACTGTAGCCACATGATTGGGAGTGGACACCTGCAGTCTCTGCAG  104
  1    GluGluValSerGluTyrCysSerHisMETIleGlySerGlyHisLeuGlnSerLeuGln

CGGCTGATTGACAGTCAGATGGAGACCTCGTGCCAAATTACATTTGAGTTTGTAGACCAG  164
 21    ArgLeuIleAspSerGlnMETGluThrSerCysGlnIleThrPheGluPheValAspGln

GAACAGTTGAAAGATCCAGTGTGCTACCTTAAGAAGGCATTTCTCCTGGTACAAGACATA  224
 41    GluGlnLeuLysAspProValCysTyrLeuLysLysAlaPheLeuLeuValGlnAspIle

ATGGAGGACACCATGCGCTTCAGAGATAACACCCCCAATGCCATCGCCATTGTGCAGCTG  284
 61    METGluAspThrMETArgPheArgAspAsnThrProAsnAlaIleAlaIleValGlnLeu

CAGGAACTCTCTTTGAGGCTGAAGAGCTGCTTCACCAAGGATTATGAAGAGCATGACAAG  344
 81    GlnGluLeuSerLeuArgLeuLysSerCysPheThrLysAspTyrGluGluHisAspLys

GCCTGCGTCCGAACTTTCTATGAGACACCTCTCCAGTTGCTGGAGAAGGTCAAGAATGTC  404
101    AlaCysValArgThrPheTyrGluThrProLeuGlnLeuLeuGluLysValLysAsnVal

TTTAATGAAACAAAGAATCTCCTTGACAAGGACTGGAATATTTTCAGCAAGAACTGCAAC  464
121    PheAsnGluThrLysAsnLeuLeuAspLysAspTrpAsnIlePheSerLysAsnCysAsn

AACAGCTTTGCTGAATGCTCCAGCCAAGATGTGGTGACCAAGCCTGATTGCAACTGCCTG  524
141    AsnSerPheAlaGluCysSerSerGlnAspValValThrLysProAspCysAsnCysLeu

TACCCCAAAGCCATCCCTAGCAGTGACCCGGCCTCTGTCTCCCCTCATCAGCCCCTCGCC  584
161    TyrProLysAlaIleProSerSerAspProAlaSerValSerProHisGlnProLeuAla

CCCTCCATGGCCCCTGTGGCTGGCTTGACCTGGGAGGACTCTGAGGGAACTGAGGGCAGC  644
181    ProSerMETAlaProValAlaGlyLeuThrTrpGluAspSerGluGlyThrGluGlySer

TCCCTCTTGCCTGGTGAGCAGCCCCTGCACACAGTGGATCCAGGCAGTGCCAAGCAGCGG  704
201    SerLeuLeuProGlyGluGlnProLeuHisThrValAspProGlySerAlaLysGlnArg

CCACCCAGGAGCACCTGCCAGAGCTTTGAGCCGCCAGAGACCCCAGTTGTCAAGGACAGC  764
221    ProProArgSerThrCysGlnSerPheGluProProGluThrProValValLysAspSer

ACCATCGGTGGCTCACCACAGCCTCGCCCCTCTGTCGGGGCCTTCAACCCCGGGATGGAG  824
241    ThrIleGlyGlySerProGlnProArgProSerValGlyAlaPheAsnProGlyMETGlu

GATATTCTTGACTCTGCAATGGGCACTAATTGGGTCCCAGAAGAAGCCTCTGGAGAGGCC  884
261    AspIleLeuAspSerAlaMETGlyThrAsnTrpValProGluGluAlaSerGlyGluAla

AGTGAGATTCCCGTACCCCAAGGGACAGAGCTTTCCCCCTCCAGGCCAGGAGGGGGCAGC  944
281    SerGluIleProValProGlnGlyThrGluLeuSerProSerArgProGlyGlyGlySer

ATGCAGACAGAGCCCGCCAGACCCAGCAACTTCCTCTCAGCATCTTCTCCACTCCCTGCA 1004
301    METGlnThrGluProAlaArgProSerAsnPheLeuSerAlaSerSerProLeuProAla

TCAGCAAAGGGCCAACAGCCGGCAGATGTAACTGGTACAGCCTTGCCCAGGGTGGGCCCC 1064
321    SerAlaLysGlyGlnGlnProAlaAspValThrGlyThrAlaLeuProArgValGlyPro
```

FIG. 2-1

```
     GTGAGGCCCACTGGCCAGGACTGGAATCACACCCCCCAGAAGACAGACCATCCATCTGCC 1124
341  ValArgProThrGlyGlnAspTrpAsnHisThrProGlnLysThrAspHisProSerAla

CTGCTCAGAGACCCCCCGGAGCCAGGCTCTCCCAGGATCTCATCACTGCGCCCCCAGGGC 1184
361  LeuLeuArgAspProProGluProGlySerProArgIleSerSerLeuArgProGlnGly

CTCAGCAACCCCTCCACCCTCTCTGCTCAGCCACAGCTTTCCAGAAGCCACTCCTCGGGC 1244
381  LeuSerAsnProSerThrLeuSerAlaGlnProGlnLeuSerArgSerHisSerSerGly

AGCGTGCTGCCCCTTGGGGAGCTGGAGGGCAGGAGGAGCACCAGGGATCGGAGGAGCCCC 1304
401  SerValLeuProLeuGlyGluLeuGluGlyArgArgSerThrArgAspArgArgSerPro

GCAGAGCCAGAAGGAGGACCAGCAAGTGAAGGGGCAGCCAGGCCCCTGCCCCGTTTTAAC 1364
421  AlaGluProGluGlyGlyProAlaSerGluGlyAlaAlaArgProLeuProArgPheAsn

TCCGTTCCTTTGACTGACACAGGCCATGAGAGGCAGTCCGAGGGATCCTCCAGCCCGCAG 1424
441  SerValProLeuThrAspThrGlyHisGluArgGlnSerGluGlySerSerSerProGln

CTCCAGGAGTCTGTCTTCCACCTGCTGGTGCCCAGTGTCATCCTGGTCTTGCTGGCCGTC 1484
461  LeuGlnGluSerValPheHisLeuLeuValProSerValIleLeuValLeuLeuAlaVal

GGAGGCCTCTTGTTCTACAGGTGGAGGCGGCGGAGCCATCAAGAGCCTCAGAGAGCGGAT 1544
481  GlyGlyLeuLeuPheTyrArgTrpArgArgArgSerHisGlnGluProGlnArgAlaAsp

TCTCCCTTGGAGCAACCAGAGGGCAGCCCCTGACTCAGGATGACAGACAGGTGGAACTG 1604
501  SerProLeuGluGlnProGluGlySerProLeuThrGlnAspAspArgGlnValGluLeu

CCAGTGTAGAGGGAATTCTAAGACCCCTCACCATCCTGGACACACTCGTTTGTCAATGTC 1664
521  ProVal...

CCTCTGAAAATGTGACGCCCAGCCCCGGACACAGTACTCCAGATGTTGTCTGACCAGCTC 1724
     AGAGAGAGTACAGTGGGACTGTTACCTTCCTTGATATGGACAGTATTCTTCTATTTGTGC 1784
     AGATTAAGATTGCATTAGTTTTTTTTCTTAACAACTGCATCATACTGTTGTCATATGTTGA 1844
     GCCTGTGGTCTATTAAAACCCCTAGTTCCATTTCCCATAAACTTCTGTCAAGCCAGACCA 1904
     TCTCTACCCTGTACTTGGACAACTTAACTTTTTTAACCAAAGTGCAGTTTATGTTCACCT 1964
     TTGTTAAAGCCACCTTGTGGTTTCTGCCCATCACCTGAACCTACTGAAGTTGTGTGAAAT 2024
     CCTAATTCTGTCATCTCCGTAGCCCTCCCAGTTGTGCCTCCTGCACATTGATGAGTGCCT 2084
     GCTGTTGTCTTTGCCCATGTTGTTGATGTAGCTGTGACCCTATTGTTCCTCACCCCTGCC 2144
     CCCCGCCAACCCCAGCTGGCCCACCTCTTCCCCCTCCCACCCAAGCCCACAGCCAGCCCA 2204
     TCAGGAAGCCTTCCTGGCTTCTCCACAACCTTCTGACTGCTCTTTTCAGTCATGCCCCTC 2264
     CTGCTCTTTTGTATTTGGCTAATAGTATATCAATTTGC
```

FIG. 2-2

30     40     50 FRACTION NO.

CONJUGATION OF POLYMER TO COLONY STIMULATING FACTOR-1

The present application is a continuation-in-part of U.S. Ser. No. 146,275, filed Jan. 20, 1988, now U.S. Pat. No. 4,847,325, issued on Jul. 11, 1989.

This invention relates to a chemical modification of biologically active colony stimulating factor-1 (CSF-1) that alters the chemical and/or physiological properties of this protein. More specifically, this invention relates to selective conjugation of CSF-1 to polymers to increase the circulating half-life of the protein in mammals.

Colony stimulating factor-1 (CSF-1) (also known as M-CSF) is one of several proteins that are capable of stimulating colony formation by bone marrow cells plated in semisolid culture medium. CSF-1 is distinguished from other colony stimulating factors by its ability to stimulate the formation of predominantly macrophage colonies. Other CSFs stimulate the production of colonies that consist of neutrophilic granulocytes and macrophages, exclusively neutrophilic granulocytes, or neutrophilic and eosinophilic granulocytes and macrophages. A review of these CSFs has been published by Dexter, T. M., *Nature* (1984) 309:746, and by Vadas, M. A., *J. Immunol* (1983) 130:793. There is currently no routine in vivo assay that is known to be specific for CSF-1 activity.

CSF-1 has been purified from native sources (see, e.g., Csejtey et al., *Biochem. Biophys. Res. Comm.* (1986) 138:238 and PCT publication No. WO 86/04587 published Aug. 14, 1986 regarding immunoaffinity chromatography of native CSF-1 to enable partial amino acid determinations). CSF-1 has also been produced from recombinant DNA using two apparently related cDNA clones: (1) a "short" form that encodes a monomeric protein of 224 amino acids preceded by a 32-amino acid signal sequence (Kawasaki et al., *Science* (1985) 230:292–296); and (2) a "long" form, encoding a monomeric protein of 522 amino acids, also preceded by the 32-amino acid signal sequence. The long form has been cloned and expressed by two groups, as disclosed in European Patent Publication No. 0272779 published Jun. 29, 1988 and Ladner et al. *EMBO J.* (1987) 6:2693, each incorporated herein by reference; and in Wong et al. *Science* (1987) 235:1504–1509, and PCT WO87/06954 published Nov. 19, 1987. (The DNA and amino acid sequences for these two clones are shown in FIGS. 1 and 2, respectively.) Both the long and short forms of CSF-1 are described by Clark and Kamen, *Science* (1987) 236:1229–1237. An "intermediate" form that encodes a monomeric protein of 406 amino acids preceded by a 32-amino acid signal sequence has also been recently reported (Cerretti et al. (1988) *Mol. Immunol.* 25:761–770).

The long and short forms of the CSF-1-encoding DNA appear to arise from a variable splice junction at the upstream portion of exon 6 of the genomic CSF-1-encoding DNA. When CSF-1 is expressed in certain eucaryotic cells from either the long or short cDNA forms, it is secreted as a dimeric glycoprotein and appears to be variably processed at the C-terminus and/or variably glycosylated. Consequently, CSF-1 proteins of varying molecular weights are found when the reduced monomeric form is subjected to Western analysis.

The amino acid sequences of the long and short forms, as predicted from the DNA sequence of the isolated clones and by their relationship to the genomic sequence, are identical in the first 149 amino acids at the N-terminus after signal peptide cleavage, and diverge thereafter as a result of the insertion in the longer clone of an additional 894 bp fragment (encoding 298 additional amino acids) before the codon encoding amino acid 150. Therefore, both the shorter and longer forms of the gene encode regions of identical sequence at the C-terminus, as well as at the N-terminus. Biologically active protein has been recovered when truncated cDNAs encoding only the first 145 or 147 amino acids of the mature short form (European Patent Publication No. 0261592 published Mar. 30, 1988; Cerretti et al. supra or the first 190 or 221 amino acids of the mature longer form, are expressed in eucaryotic cells.

Recombinant CSF-1 was expressed in *E. coli* by modifying a short clone cDNA originally described by Kawasaki et al., *Science* (1985) 230:291 to code for proteins that contained 1) the native N-terminus and a C-terminus at amino acid 150 of the mature protein, and 2) a truncation to delete the first two amino acids at the N-terminus and a C-terminus at amino acid 150 of the mature protein. These proteins were purified and refolded to form homodimers and were found to have apparent molecular weights on size-exclusion high performance liquid chromatography (HPLC) of about 43,000 and 40,000 daltons, respectively. CSF-1 proteins modified so that the C-terminus of the expressed protein is amino acid 150 or 158 and so that up to three amino acids at the N-terminus are deleted have also been prepared.

Small proteins (less than about 70 kd) often have a relatively short half-life in blood after intravenous injection. Rapid clearance of drugs from circulation often reduces their efficacy. It is often desirable to increase the half-life of a circulating polypeptide so that smaller amounts of the polypeptide or less frequent injections might be administered, while retaining the desired therapeutic effect. Modifications of the CSF-1 protein that might alter its half-life in vivo, reduce its immunogenicity, or reduce or eliminate aggregation of the protein that might occur when it is introduced in vivo would be desirable. Such modifications include the modification of proteins with substantially straight chain polymers such as polyethylene glycol (PEG), polypropylene glycol (PPG), dextran, or polyvinyl alcohol.

For example, U.S. Pat. No. 4,261,973 describes conjugation of immunogenic allergen molecules with non-immunogenic water-soluble polymers such as PEG or polyvinyl alcohol to reduce the immunogenicity of the allergen. U.S. Pat. No. 4,301,144 describes conjugation of hemoglobin to PEG, PPG, a copolymer of ethylene glycol with propylene glycol, or ethers, esters or dehydrated products of such polymers to increase the oxygen-carrying ability of the hemoglobin molecule. U.S. Pat. No. 4,609,546 discloses that conjugation of a polypeptide or glycoprotein such as a colony stimulating factor to a polyoxyethylene-polyoxypropylene copolymer may increase the duration of its physiological activity. The only proteins that have been tested in this fashion are enzymes or native interferon, which are readily water-soluble. PCT WO 86/04145 published Jul. 17, 1986 discloses PEG modification of antibodies to decrease binding to Fc receptors. U.S. Pat. No. 4,179,337 discloses conjugation of water-soluble polypeptides such as enzymes and insulin to PEG or PPG to reduce the immunogenicity of the polypeptides while retaining a substantial proportion of their desired physiological activities. EP 154,316, published Sep. 11, 1985 to Takeda Chemical Industries, Ltd., discloses and claims chemically modified lymphokines such as IL-2 containing PEG bonded directly to at least one primary amino group of the lymphokine. In addition, Katre et al., *Proc. Natl. Acad. Sci.* (1987) 84:1487 discloses modification of IL-2 with PEG.

Many other references disclose the concept of PEG derivatization of proteins such as alpha-1-proteinase inhibitor, asparaginase, uricase, superoxide dismutase, streptokinase, plasminogen activator, IgG, albumin, lipoprotein lipase, horseradish peroxidase, catalase, arginase and asparaginase, as well as peptides. Such derivation through lysines was reported as improving half-life, decreasing immunogenicity, increasing solubility, and in general, increasing efficacy (which permitted less frequent dosing). In most cases, the proteins required multiple modifications per molecule to achieve improved performance in vivo, and the activity in vitro was significantly decreased by such modification.

Modification of IL-2, IFN-$\beta$ and immunotoxins with PEG through cysteine residues of a polypeptide is disclosed in PCT WO87/00056 published Jan. 15, 1987.

In addition to these patents and patent publications, several articles discuss the concept of using activated PEG or PPG as a modifying agent for proteins such as enzymes, IgG and albumin. For example, Inada et al., *Biochem. and Biophys. Res. Comm.*, 122, 845–850 (1984) disclose modifying water-soluble lipoprotein lipase to make it soluble in organic solvents such as benzene by using cyanuric chloride to conjugate with PEG. Takahashi et al., *Biochem. and Biophys. Res. Comm.*, 121:261–265 (1984) disclose modifying horseradish peroxidase using cyanuric chloride triazine with PEG to make the water-soluble enzyme active and soluble in benzene.

Patents and patent publications that disclose use of polyvinyl alcohol (PVA) in protein conjugation reactions include U.S. Pat. Nos. 4,296,097 and 4,430,260, relating to conjugation of benzylpenicillin and PVA, U.S. Pat. No. 4,496,689 (EP 147,761), relating to conjugation of alpha-1-proteinase inhibitor with a polymer such as heparin, PVA or PEG, EP 142,125 published May 22, 1985, disclosing non-covalent bonding of hemoglobin to PVA as a carrier, DE 2312615 (Exploaterings AB TBF), relating to crosslinked, water-insoluble PVA coupled to a protein, and DE 3,340,592 published May 23, 1985, relating to conjugates of PVA with human hemoglobin A.

Articles relating to conjugates of proteins and PVA include Sabet et al., *Indian J. Chem.*, A (1984) 23A(5) (disclosing PVA and protein interaction), Wei et al., *Immunol.* (1984) 51(4):687–696 (disclosing trimellityl conjugated with PVA), Lee et al., *J. Immunol.* (1981) 126:414–418 and Hubbard et al., *J. Immunol.* (1981) 126:407–413 (both disclosing DNP conjugated to PVA), Lee et al., *Int. Arch. Allergy Appl. Immunol.* (1980) 63:1–13 (disclosing antibenzylpenicilloyl IgE conjugated to PVA), Sehon, *Prog. Allergy* (1982) 32:161–202 (disclosing an allergen and hapten conjugated via PVA), Holford-Strevens et al., *Int. Arch. Allergy App. Immunol.* (1982) 67:109–116 (disclosing conjugation of PVA and an antigen/hapten), and Sehon and Lee, *Int. Arch. Allergy App. Immunol.* (1981) 66 (Supp. 1), p. 39–42 (disclosing a hapten/allergen conjugated to PVA).

PCT Publication Nos. WO 86/04607 and WO 87/03204 and Ralph et al., *Immunobiol.* (1986) 172:194 disclose various potential uses of CSF-1, including use as an anti-infection, anti-tumor, or wound-healing agent.

None of these references, however, discloses details of how to modify CSF-1 with a polymer such as PEG or polyvinyl alcohol so as to retain its biological activity while also increasing its circulating half-life or efficacy. Furthermore, it is not generally possible to predict the extent of protein modification or the nature of the reaction conditions that are desirable, because some proteins are much more susceptible to inactivation through conjugation than others.

Accordingly, the present invention provides for modifying colony stimulating factor-1 to increase its half-life in vivo, while also retaining useful biological activity. The modified CSF-1 may be used to stimulate cells in vivo at much reduced and/or less frequent dosage than the unmodified CSF-1.

As secondary advantages, the modification may decrease the immunogenicity of the CSF-1 (especially when used in heterologous species, such as use of human CSF-1 for cattle) and/or reduce aggregation of the protein that might occur.

More specifically, the present invention is directed to a biologically active composition having prolonged in vivo half-life in mammals, comprising a protein that stimulates the formation of primarily macrophage colonies in the in vitro colony stimulating factor-1 assay, which protein is covalently conjugated to a water-soluble polymer selected from the group consisting of polyethylene glycol or polypropylene glycol homopolymers, polyoxyethylated polyols, and polyvinyl alcohol, wherein said homopolymer is unsubstituted or substituted at one end with an alkyl group. The CSF-1 protein may be conjugated to the polymer via: (1) free amino groups, including lysine residues and the N-terminal amino acid (preferably 1 to 3 sites), (2) carbohydrate moiety(ies) of eukaryote-expressed, glycosylated CSF-1; or (3) free sulfhydryl groups engineered into the CSF-1

Preferably the polymer is unsubstituted polyethylene glycol (PEG), monomethyl PEG (mPEG), or polyoxyethylated glycerol (POG) that is coupled to the (1) lysine residue(s) of the CSF-1 via an amide or urethane linkage formed from an active ester (preferably the N-hydroxysuccinimide or paranitrophenyl ester) of a PEG, mPEG, or POG carboxylic or carbonic acid; (2) carbohydrate moiety(ies) of the CSF-1 via an amine, hydrazine, or hydrazide linkage; or (3) cysteine residue(s) of the CSF-1 via a maleimido or haloacetyl (where halo is Br, Cl or I) group.

Another aspect of this invention resides in a process for preparing the conjugated protein described above, comprising:

(a) providing a water-soluble polymer having at least one terminal reactive group where the polymer is selected from the group consisting of polyethylene or polypropylene glycol homopolymers and polyoxyethylated polyols, and polyvinyl alcohol, wherein said homopolymer is unsubstituted or substituted at one end with an alkyl group;

(b) reacting the protein with the reactive group of said polymer so as to render the protein biologically active and selectively conjugated; and (c) purifying the conjugated protein.

In another aspect, the invention relates to a method for prophylactic or therapeutic treatment of infectious diseases or cancer in mammals and to a methods effective for cancer treatment, osteroporesis treatment, wound healing, cholesterol lowering or antibody dependent cellular cytotoxicity (ADCC) in mammals comprising administering to the mammal an effective amount of a pharmaceutical preparation comprising the conjugated CSF-1 protein dissolved in a pharmaceutically acceptable aqueous carrier medium.

BRIEF DESCRIPTION OF THE DRAWINGS

FIGS. 1-1 and 1-2 show the cDNA and deduced amino acid sequence for pCSF-17 (32 amino acid leader sequence and amino acids 1–224).

FIGS. 2-1 and 2-2 show the cDNA and deduced amino acid sequence for CSF-4 (partial amino acid leader sequence and amino acids 1–522).

DEFINITIONS

Figure 3A:
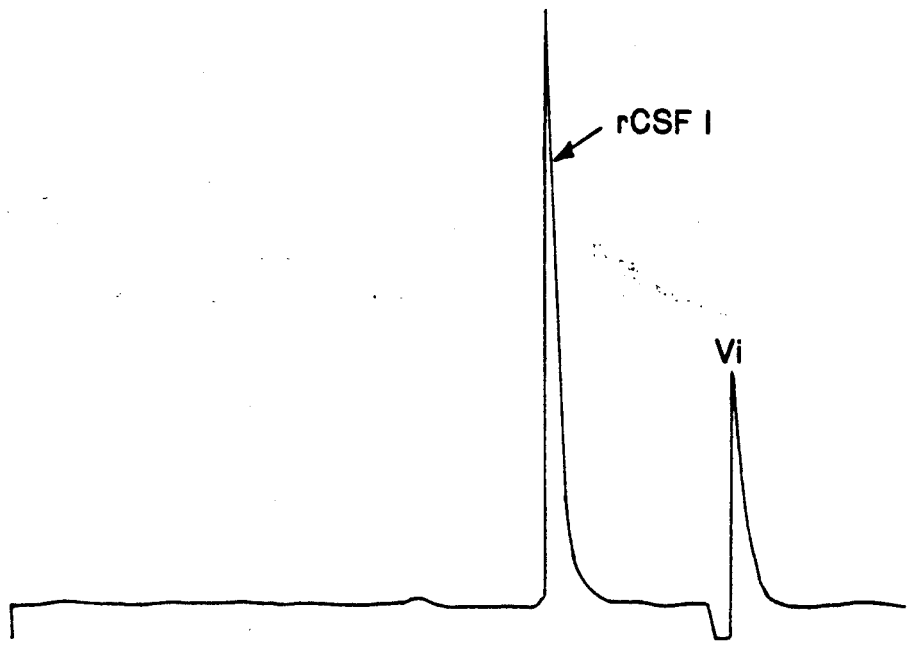
FIG. 3A shows the size exclusion HPLC chromatogram of underivatized recombinant CSF-1 (rCSF-1) (SCSF/N∇2C∇150).

"Colony stimulating factor-1" refers to a dimeric protein or glycoprotein composition that has the biological activity for CSF-1 in the standard in vitro colony stimulating assay of Metcalf. J. Cell. Physiol. (1970) 76:89 wherein the polypeptide stimulates the formation of primarily macrophage colonies. "Biologically active CSF-1" means a composition of conjugated CSF-1, that has essentially the same specific activity in mouse bone marrow colony-forming assays as the unconjugated form of the same CSF-1 or at least about 10% of its specific activity. A "native" CSF-1 is a non-recombinant CSF-1. Murine CSF-1 is described in European Patent Publication No. 0272779, Rajavashisth et al., Proc. Natl. Acad. Sci. USA (1987) 84:1157 and in DeLamarter et al., Nucleic Acids Res. (1987) 15:2389.

"Clinically pure" CSF-1 means a preparation of biologically active human CSF-1 produced recombinantly in bacteria that is at least 95% CSF-1 either by RP-HPLC or by either reducing or non-reducing SDS-PAGE analysis and has an endotoxin content of less than about 1.0 ng/mg CSF-1.

"Selectively conjugated" refers to proteins that are covalently bonded via free amino groups of the protein (preferably one or two free amino groups, to retain maximum biological activity), via free sulfhydryl groups (if any), or via a carbohydrate moiety (if any) present in the protein.

"Effective amount" and "immunotherapeutically effective amount" signify an amount effective to perform the function specified, such as to promote tumor reduction or prevent or cure infections diseases. The exact optimal amount will depend on many factors, including the patient's clinical history and current disease, the schedule, the route, and the response of the patient.

"Therapeutic treatment" indicates treating after the disease is contracted, whereas "prophylactic" treatment indicates treating to prevent contraction of the disease.

"Mammals" indicates any mammalian species, and includes rabbits, mice, dogs, cats, cattle, sheep, primates, and humans, preferably humans.

"Muteins" are genetically engineered proteins expressed from a nucleic acid sequence that has been altered using techniques such as sito-specific mutagenesis. Such genetic alterations are designed to result in one or more substitutions, additions, and/or deletions to the amino acid sequence of the parent protein.

"Pharmaceutically acceptable" refers to a carrier medium that does not interfere with the effectiveness of the biological activity of the active ingredient(s), is stable, and is not toxic to the host to whom it is administered.

"Homodimer" refers to a dimeric protein essentially identical in its two subunits except that it also includes dimeric proteins with minor microheterogeneities that occasionally arise on production or processing of recombinant proteins.

"Heterodimer" refers to a dimeric protein having subunits which differ in amino acid sequence, the number of amino acids or both. In other words, heterodimers have two nonidentical subunits.

CSF-1 Proteins

As set forth in the background section, CSF-1 is biologically active in its dimeric form. The CSF-1 employed herein may be the native dimer or recombinantly produced dimer. Native dimeric CSF-1 species have been obtained from human urine, cultured monocytes, and culture supermatants of some cell lines. It has been possible to obtain recombinant DNA encoding CSF-1 monomers consisting of a variety of amino acid sequences and lengths. FIGS. 1 and 2 show the DNA sequences and amino acid sequences predicted from the DNA sequences for, respectively, the full-length, unprocessed short and long forms, both of which contain a 32-amino acid signal sequence at their N-termini. The sequences of the monomeric CSF-1 protein are considered herein for convenience to be the 224-amino-acid short form without the leader sequence (designated herein as SCSF), and the 522-amino-acid long form without the leader sequence (designated herein as LCSF). Other CSF-1 dimers produced from DNA sequences modified by point mutation(s), insertion(s), deletion(s), and/or translocation(s) are also expected to benefit from the chemical modification of this invention if they are biologically active.

The recombinant CSF-1, produced in any host, whether eukaryotic or prokaryotic, may be conjugated to polymers via selected amino acid side groups, preferably free amino groups. Preferably, the DNA encoding CSF-1 is expressed in bacteria and the resulting CSF-1 is a homodimer after purification and refolding. If the conjugation is via a carbohydrate moiety, the host may be eukaryotic, or glycosylation may be carried out in vitro.

For convenience, the primary structure of the protein subunits encoded by the various cDNA constructs described will be designated herein using a shorthand notation, as follows: LCSF denotes the 522-amino acid sequence disclosed for the clone CSF-4, set forth in European Patent Publication No. 0272779 referred to above and shown in FIG. 2, without the complete signal sequence. SCSF denotes the 224-amino acid sequence disclosed for the clone pCSF-17, shown in FIG. 1, without the signal sequence, described in the Kawasaki article referred to above, Science (1985) 230:292-296, also incorporated herein by reference.

It will be noted that one particular pCSF-17 clone derivative has an aspartic acid residue at position 59. The disclosed LCSF clone also encodes Asp at position 59. Muteins corresponding to amino acid substitutions within the sequences depicted in FIGS. 1 and 2 are correspondingly designated by the substitution subscripted with the position. Mutein forms of CSF-1 are disclosed in European Patent Publication No. 0272779 published Jun. 29, 1988, the disclosure of which is incorporated herein by reference. When constructs encoding these proteins are expressed in bacteria, the final products may also retain N-terminal methionine to varying degrees. Since the extent of N-terminal methionine removal cannot be reliably predicted, this possibility is not included in the notation.

C-terminal and N-terminal truncations of these basic SCSF and LCSF sequences will be designated as C∇ or N∇, respectively. The C-terminal deletions will be followed by the number representing the number of amino acids of the native structure remaining; for the N-terminal deletions, N∇ will be followed by the number of amino acids deleted from the N-terminus. Thus, for example, LCSF/C∇150 denotes a construct encoding a protein that contains the first 150 amino acid residues of the long CSF sequence; SCSF/C∇158 denotes a construct encoding a protein that contains the first 158 amino acid residues of the short form; SCSF/N∇2 denotes a construct encoding the short form with two N-terminal amino acids deleted. (As set forth above, the LCSF and SCSF diverge beginning at position 150 and reconverge after 298 amino acids in the LCSF clone). LCSF/N∇2C∇150 denotes a form that is the same as LCSF/C∇150, except that the two N-terminal glutamic acid residues are deleted.

Plasmids encoding a variety of CSF-1 forms are currently available, and can be expressed in bacterial systems. A form of plasmid encoding the long form of CSF-1 can be expressed in eukaryotic cells, in which case, the eukaryotic cell "processes" the clone, secreting a protein that is C-terminally truncated and has the leader sequence removed from the N-terminus. Alternatively, the clone can be truncated to express specific C-terminally deleted forms in eukaryotic or prokaryotic cells. In addition, the first two or three N-terminal codons can be deleted so that the resulting protein expressed in $E.\ coli$ is more homogeneous. Specifically, the N-terminal methionine encoded just upstream of the mature native sequence N-terminus in the $E.\ coli$ constructs (which is retained in the protein as "N-terminal Met" unless removed by post-translational processing) is more readily removed from these N-terminal deletion constructs. Furthermore, significant heterogeneity detectable using reverse-phase HPLC (RP-HPLC) is found when the gene encoding the "native" N-terminal sequence (for example, of the short form, mutein SCSF/C∇150) is expressed in $E.\ coli$ and the purified product is characterized. This heterogeneity is eliminated when the corresponding CSF-1 gene lacking the two N-terminal codons (glutamic acid) is expressed. Correspondingly, N-terminal truncated forms of other short and long CSF-1 gene constructs can also be employed.

Preferred constructions are those wherein the protein consists essentially of an amino acid sequence selected from the group consisting of LCSF/C∇150 through C∇464, tyr$_{59}$LCSF/C∇150 through C∇464; asp$_{59}$SCSF/C∇150 through C∇166. More preferred are those CSF-1 proteins consisting essentially of an amino acid sequence selected from the group consisting of LCSF/C∇150; LCSF/C∇190; LCSF/C∇221; LCSF/C∇223; LCSF/C∇236; LCSF/C∇238; LCSF/C∇249; LCSF/C∇258; LCSF/C∇406; LCSF/C∇411; LCSF/C∇464; asp$_{59}$SCSF/C∇150; asp$_{59}$SCSF/C∇153; and asp$_{59}$SCSF/C∇158.

Particular preferred constructions that result in CSF-1 proteins for modification herein include clones encoding LCSF/C∇190, LCSF/C∇221, asp$_{59}$SCSF/C∇158, asp$_{59}$SCSF/C∇150 and their corresponding N∇2 and N∇3 forms.

The most preferred starting materials are the products of the clones encoding asp$_{59}$SCSF/C∇150; asp$_{59}$SCSF/C∇158; LCSF/C∇221 and their corresponding N∇3 forms.

Alternatively, the CSF-1 may be in the form of a heterodimer prepared from among various monomeric units of CSF-1, particularly if the conjugation is done through a reactive cysteine residue of the CSF-1 heterodimer. The large number of CSF-1 proteins formed by variations in C-terminal sequence due either to differences in processing or clone construction provides a variety of starting materials that can be utilized in heterodimer formation. Thus, novel heterodimeric materials can be formed by refolding. For example, the monomeric form of SCSF/C∇150, along with the monomeric form of LCSF/C∇157, can be mixed and treated according to the method of PCT Publiction No. WO 88/08003 published Oct. 20, 1988, the disclosure of which is incorporated herein by reference. The heterodimer can then be separated from the homodimeric and oligomeric side products by various chromatographic and other methods. The heterodimer (particularly SCSF/C∇150 and LCSF/C∇157) can be made to terminate on one subunit at the 157 position, providing a potentially free sulfhydryl group for reaction with the conjugation polymer. Similar mixtures subjected to the method of the invention could lead to heterodimers of components having amino acid substitutions—e.g., glu$_{52}$LCSF/C∇221 and LCSF/C∇190.

The differing monomers may be mixed in vitro or produced in the same cell. If produced in the same cell, a construct for expression of each monomer is introduced into the same host; in such embodiments, it is preferred that each construct bear a different marker (such as tetracycline resistance (Tc ®) and Ampicillin resistance (Amp ®), so that cotransformed hosts are selected. The cotransformed cells are then grown and induced to obtain mixtures of the two forms.

In addition, single cysteine residues can be engineered into CSF-1 in a non-natural location to create a construct of rCSF-1 containing a free sulfhydryl group on a cysteine residue for PEG reaction, provided the molecule retains bioactivity. Heterodimer constructs containing a substitution of a given cysteine in only one of the two subunits may also be useful in the generation of free sulfhydryls. Also, carbohydrate moieties can be placed on the CSF-1 protein, either by expression from eukaryotic systems or by in vitro glycosylation with enzymes.

Recombinant CSF-1 proteins may or may not retain the exact length prescribed by the clone, due to processing by the host. Therefore, although the starting material proteins are referred to by the same designation, it should be understood that these designations, in reality, refer to the clone construct, and the actual length of the starting material for the process disclosed herein may be shorter, or longer (if it has N-terminal Met), than that specified by the C-terminal amino acid number.

As mentioned above, the CSF-1 may be produced in eukaryotic cells, e.g., mammalian, insect, or yeast cells. Production in mammalian cells is described in PCT Patent Publication No. WO 86/04607. The CSF-1 may be produced from insect cells using a baculovirus vector, as described in Luckow et al., *Biotechnol*, (1988) 6:47, the disclosure of which is incorporated herein by reference. Other descriptions of this type of CSF-1 production are contained within Weaver et al., *Bio/Technology* (1988) 6:287. Insect-cell-produced CSF-1 (SCSF/C∇ 150) is a glycosylated dimer that was found to have a very short in vivo half-life. The two N-linked glycosylation signals in the amino acid sequence of SCSF (Asn 122 and Asn 140) could be modified in the DNA using site-directed mutagenesis to generate a non-glycosylated, bioactive insect-cell-produced CSF-1 protein (Gln 122, Gln 140). This protein can then be reacted via its lysine or cysteine residues with a polymer as done with prokaryote-expressed rCSF-1 to increase its in vivo half-life.

The polymer can be attached covalently to the glycosylated CSF-1 on the carbohydrate, by reacting, for example, PEG-amine, PEG-hydrazine, or PEG-hydrazide with CSF-1 protein that has been oxidized with periodate to convert vicinal diols of the sugars to aldehydes. The PEG-amine can be prepared by converting PEG-OH to PEG-tosylate and then to PEG-phthalimide, and the phthalimide is cleaved with hydrazine to produce PEG-$NH_2$ in a Gabriel synthesis. PEG-hydrazine and PEG-hydrazide can be prepared by methods known to those skilled in the art. The PEG derivative will couple at carbohydrate sites where vicinal diols were converted to aldehydes.

If CSF-1 is produced intracellularly in bacterial hosts, it must be refolded to form active dimers in high yield, as described in PCT Publication No. WO 88/08003 supra. Briefly, in this procedure the solubilized monomer, whether secreted or produced as a mature or fusion protein, is maintained in a chaotropic environment under reducing conditions. Such maintenance involves the use of a suitable reducing agent such as β-mercaptoethanol or dithiothreitol (DTT). The solubilized protein is typically maintained in, for example 8M urea or 7M guanidinium hydrochloride, at a pH of about 7–8.6, in the presence of about 2–100 mM thiol compound. Starting with this solubilized form, the monomer may either be refolded directly or purified from remaining proteins by a suitable purification procedure such as chromatography on an adsorbant gel, chromatography using an ion exchange column, or gel-permeation chromatography prior to refolding. Gel-permeation chromatography is useful, as it permits an easy size separation of the desired monomer length, which is generally known in advance, from impurities of differing molecular weights. DEAE Sepharose chromatography in urea is even more useful, as it concentrates as well as purifies and is more easily scaled up than is sizing. It is preferable that the purification be conducted under reducing conditions to prevent the formation of disulfide-linked aggregates.

Thus, regardless of the chromatographic procedure used, a suitable reducing agent is included in the solutions used to load the chromatographic columns or batches and in the eluting solutions. In some instances, low pH may be substituted for reducing agent, as low pH will essentially prevent disulfide bond formation and is compatible with some chromatographic systems. In addition, inclusion of a low concentration of a chelating agent may help to preserve the reduced form of the protein.

The partially purified monomer is then subjected to refolding conditions for the formation of the dimer. The protein concentration during this step is of considerable importance. Generally, final percent yields per volume of the CSF-1 refolding reaction are increased if the protein concentration is less than about 2 mg/ml of the CSF-1 protein; a concentration range of 0.03–1.0 mg/ml is preferred. The refolding conditions may include gradual removal of the chaotropic environment over an appropriate time period, usually several hours, or dilution of the sample to the desired concentration of protein and chaotropic agent. Also possible are methods that provide a constant protein concentration, such as dialysis or hollow fiber diafiltration, while the chaotrope is slowly removed. At the end of the process, when the chaotrope is depleted, a relatively non-denaturing level is reached. For example, if guanidine hydrochloride is used as a chaotrope, a final concentration of less than about 2M, and preferably 0.1–1M, is attained, and if urea is used as the chaotrope, a final concentration of less than about 1M, and preferably 0.1–0.5M, is attained.

The refolding is conducted so as to permit oxidation of the sulfhydryl groups to disulfides that establish the biologically active dimeric configuration that, in the case of CSF-1, requires the formation of disulfide bonds, one or more of which links the two chains. One or more intrachain disulfides are also formed. Suitable redox conditions that encourage this formation of dimers include the sulfhydryl/disulfide reagent combinations, such as oxidized and reduced glutathione. The ratio of reduced to oxidized glutathione or other sulfhydryl/disulfide combination is typically from about 2 mM/0.1 mM to 0.5 mM/1.0 mM. Other methods of oxidation are also acceptable. In any event, the pH of the solution during the refolding process should be maintained at about 7.5 to 9.0 to favor the reaction. It is clear that during the process of refolding the highly reducing conditions under which the initial purification was conducted are no longer employed. The exclusion of significant concentrations of salts, such as sodium chloride, during the refolding process, permits the use of ion exchange chromatography as a subsequent concentration/purification step.

During the refolding process higher oligomeric species of CSF-1 may be formed. This aggregation process is minimized through temperature control, wherein low temperatures of about 0°–4° C. are preferable to higher temperatures of 25°–37° C.

Residual redox reagents present in the refolded CSF-1 preparation may possibly facilitate disulfide exchanges during subsequent purification steps. Two more preferred procedures to block such unwanted disulfide exchanges include lowering the pH to below 7.0 or diafiltration to remove the redox reagents.

For example, prior to further purification of the refolded, dimeric CSF-1, removal of the redox material and concentration of the refolded proteins may be performed by direct loading of the refolded material onto an ion exchange chromatography column using, for example, DEAE Sepharose. Frequently such procedures are carried out at pHs around 8; however, lowering the pH into the range of 5.5 to 7.0 reduced oligomer formation and increased yield of dimeric CSF-1.

After refolding, concentration, and purification, the dimer is further purified from residual redox material and from other proteins using procedures similar to those set forth above for the monomer. Suitable means, in particular, include gel filtration, hydrophobic interaction chromatography, ion exchange chromatography, and reverse-phase HPLC.

A particularly successful protocol for removal of undesirable impurities such as pyrogens or other endotoxins includes the use of chromatography on a phenyl-TSK or phenyl-Sepharose column. The chromatography is carried out under conditions and with reagents that are essentially endotoxin-free. The desired dimeric CSF-1 is soluble and stable in approximately 1.5M ammonium sulfate at neutral pH, and is loaded onto the columns under these conditions at low temperatures, i.e., from about 4° C. to about 10° C., and preferably about 4° C. Removing the precipitate that forms on adding the ammonium sulfate removes some aggregates and unstable forms of refolded CSF-1. The CSF-1 protein can be eluted using a gradient of decreasing ammonium sulfate (1.5 to 0M) with increasing ethylene glycol (0 to 50%) in neutral buffer. The CSF-1 dimer elutes at approximately 0.6M ammonium sulfate, 35% ethylene glycol from the phenyl-TSK column. Propylene glycol may be used instead of ethylene glycol, in which case the elution conditions will be somewhat different. Alternative supports can also be used, and phenyl-Sepharose is, in fact, preferred for larger scale production of the purified CSF-1 dimeric protein.

Conjugation

The CSF-1 protein described above is conjugated to the polymer via either (1) free amino group(s), preferably only one or two in order to minimize loss of biological activity, (2) at least one carbohydrate moiety on the protein, or (3) free sulfhydryl group(s) that is/are engineered into the clone and remain free after refolding.

The number of polymer molecules that have been conjugated to the protein can be determined by various methods, including, for example, acid degradation or digestion, followed by amino acid analysis if the links are maleimido or bromoacetyl to cysteine links and the extent of derivatization is high (more than 4 moles/mole). Alternatively, the conjugated protein can be digested into small fragments with an enzyme (e.g., trypsin) and separated by column chromatography. A peptide map of the protein before and after modification would be compared, and fragments with altered elution times sequenced to determine the location(s) of polymer attachments. In a third alternative, the polymer can be radioactively labeled prior to coupling to determine how many moles of radioactive polymer are attached per mole of CSF-1 protein. In cases where polymers of relatively uniform molecular weight are conjugated to CSF-1 of uniform molecular weight, measurement of the molecular weight of the conjugate can serve as an estimate of the number of polymers per CSF-1 molecule.

The residue(s) to be conjugated may be: (1) any free amino groups ($\epsilon$-amino groups at lysine residues or a free amine group, if any, at the N-terminus), (2) free sulfhydryl groups on cysteine residues that are engineered or constructed into CSF-1, or (3) carbohydrate moiety (discussed elsewhere). It has been found that if the protein is moderately derivatized on free amino groups with PEG (i.e., contains about one to three modified amino acid residues), it retains from 25–100% of the bioactivity of underivatized CSF-1. If, however, it is highly derivatized with PEG, the conjugated protein has significantly less measurable bioactivity, depending on the type of CSF-1, length of PEG polymer and the linker and reaction conditions employed.

The polymer to which the protein is attached is a homopolymer of polyethylene glycol (PEG) or of polypropylene glycol (PPG), a polyoxyethylated polyol, or polyvinyl alcohol, provided in all cases that the polymer is soluble in water at room temperature. Examples of polyoxyethylated polyols include polyoxyethylated glycerol, polyoxyethylated sorbitol, polyoxyethylated glucose, and the like.

The glycerol backbone of polyoxyethylated glycerol is the same backbone occurring naturally in, for example, animals and humans in mono-, di-, and triglycerides. Therefore, this compound might not necessarily be seen as foreign in the body.

The polymer preferably has an average molecular weight between about 1000 and 100,000 daltons, more preferably between 4000 and 40,000 daltons, depending, for example, on the molecular weight of the particular CSF-1 employed. Since the object of the modification is to obtain a conjugated protein with retained biological activity, with enhanced in vivo half-life over the unconjugated protein, and with reduced immunogenicity, the molecular weight of the polymer will be chosen to optimize these conditions, e.g., a modified dimeric CSF-1 protein of over about 80 Kd apparent molecular weight.

An additional advantage gained in derivatizing native dimeric CSF-1 (i.e., non-recombinant protein) is that the use of a scarce CSF-1 that is hard to purify would be maximized by such a modification.

Preferably the PEG homopolymer is substituted at one end with an alkyl group, but it may also be unsubstituted. Preferably the alkyl group is a $C_1$–$C_4$ alkyl group, and most preferably a methyl group. Most preferably, the polymer is a monomethyl-substituted PEG homopolymer and has a molecular weight of about 4000 to 40,000 daltons.

The covalent modification reaction may take place by any of the methods described above, preferably at about pH 5–9, more preferably 7–9 if the reactive group on the protein is a free amino group. Using the latter approach, the protein is conjugated via at least one terminal reactive group added to the polymer. The polymer with the reactive group(s) is designated herein as "activated polymer". The reactive group(s) selectively react with a free amino or other reactive group of the protein. (If there is more than one reactive group, the conjugation conditions must be carefully controlled to prevent crosslinking; however, monovalent species are preferred.) The amount of intact activated polymer employed is generally about 1- to 30-fold molar excess of the active polymer over the protein. The exact molar ratio used is dependent upon a number of variables including the type of activated polymer used, the pH, the protein concentration and the CSF-1 molecule used. For activated polymers other than the PEG-chloroformate active ester, the molar excess of activated polymer over protein is preferably no more than about 11 moles per mole of CSF-1 dimer for derivatization of amino groups, and most preferably is about 1 to 8 moles per mole of CSF-1. The molar excess of PEG-chloroformate active ester (PEG-PNP) over protein is preferably no more than about 5 moles per mole of CSF-1 dimer for derivatization of amino groups and most preferably is about 1 to 2 moles per mole of CSF-1.

Generally the process involves preparing an activated polymer and thereafter reacting the protein with the activated polymer. Typically, the reaction is carried out in a buffer of pH about 7-9, frequently at about 10 mM Hepes pH 7.5, 100 mM NaCl, if an internal-ester-free PEG-NHS reagent is used or at about 50 mM Na borate pH 9 if the PEG-PNP reagent is used, both of which are described below. The reaction is carried out generally at 0° to 25° C. for from about 20 minutes to about 12 hours, preferably 25-35 minutes at 20° C. or three hours at 4° C. Following the conjugation, the desired product is recovered and purified by column chromatography or the like.

The modification reaction with active PEG can be performed in many ways, described below, using one or more steps. Examples of suitable modifying agents that can be used to produce the activated PEG in a one-step reaction include cyanuric acid chloride (2,4,6-trichloro-S-triazine) and cyanuric acid fluoride.

In one preferred embodiment the modification reaction takes place in two steps wherein the PEG-OH is reacted first with an acid anhydride such as succinic or glutaric anhydride to form a carboxylic acid, and the carboxylic acid is then reacted with a compound capable of reacting with the carboxylic acid to form an activated PEG with a reactive ester group that is capable of reacting with the protein. Examples of such compounds include N-hydroxysuccinimide, sulfo-N-hydroxysuccinimide, 4-hydroxy-3-nitrobenzene sulfonic acid, and the like. Preferably, N-hydroxysuccinimide is used.

For example, monomethyl-substituted PEG may be reacted at elevated temperatures, preferably about 100°-110° C. for four hours, with glutaric anhydride. The monomethyl PEG-glutaric acid thus produced is then reacted with N-hydroxysuccinimide in the presence of a carbodiimide reagent such as dicyclohexyl or diisopropyl carbodiimide to produce the activated polymer, methoxypolyethylene glycolyl-N-succinimidyl glutarate, which can then be reacted with the protein after purification. This method is described in detail in Abuchowski et al., Cancer Biochem. Biophys., 7:175-186 (1984).

In another example, the monomethyl-substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described in Bhatnagar et al., *Peptides: Synthesis-Structure-Function, Proceedings of the Seventh American Peptide Symposium*, Rich, et al. (eds.) (Pierce Chemical Co., Rockford IL., 1981), p. 97-100, in Nitecki et al., *High-Technology Route to Virus Vaccines* (American Society for Microbiology: 1985), pages 43-46 (based on talk Nov. 8-10, 1984), entitled "Novel Agent for Coupling Synthetic Peptides to Carriers and Its Application", and in Aldwin et al., *Anal. Biochem.* (1987) 164:494-501. The disclosures of all of these are incorporated herein by reference.

As ester bonds are chemically and physiologically more reactive than amide bonds, it may be preferable to derivatize the protein with activated polyethylene glycol molecules that would not generate esters in the final product.

In one embodiment, the PEG may be activated for attachment to the protein using PEG-amine or PEG-OH as starting materials. The PEG-OH may be converted to the PEG-amine as described by V. N. R. Pillar et al., *J. Organic Chem.*, 45:5364-5370 (1980), the disclosure of which is incorporated herein by reference. Briefly, monomethyl PEG-amine (mPEG) is prepared by converting mPEG-OH to mPEG-tosylate and then to mPEG-phthalimide, and the phthalimide is cleaved with hydrazine to produce mPEG-NH$_2$ in a Gabriel synthesis. The mPEG-amine is then reacted with glutaric anhydride at room temperature for about four hours to produce mPEG-NHCO(CH$_2$)$_3$COOH. After the reaction the product is precipitated, purified, and reacted with N-hydroxysuccinimide and dicyclohexylcarbodiimide to produce

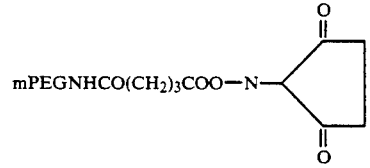

This compound can then be reacted with the appropriate free amino group(s) of the CSF-1 polypeptide.

In another embodiment, active ester forms of polyethylene glycol carboxylic acid useful for such conjugation are described in Nitecki et al., Peptide Chemistry 1987, Shiba & Sakakihara (Ed). Protein Research Foundation, Osaka (1988). Briefly, the active esters have a formula of:

 (I) or

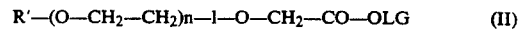 (II)

wherein R' is a lower alkyl group of 1-4 carbon atoms, R$^2$ is H or an organic substituent, n is about 8-500, LG is a leaving group selected from cyanomethyl, an aromatic group selected from a phenyl or naphthyl group substituted with from 1 to 5 substituents that render the aromatic group more labile, and a pyridyl group optionally containing 1-4 of these substituents. These esters may be produced, for Compound I, by alkylation of the polyethylene glycol with an alpha-haloalkanoic acid or ester thereof followed by esterification with HO—CH$_2$—CN or the group corresponding to LG, or, for Compound (II), by oxidation of the PEG to its acid, followed by esterification with HO—CH$_2$—CN or the group corresponding to LG. Most preferably, Formula I is prepared and the activating agent is para-nitrophenol or orthonitrophenol. Most preferably, the polymer is conjugated to the protein via an amide linkage formed from the para-nitrophenyl ester of the polymer. For example, the PEG-OH may be converted to PEG-O and reacted with $BrCH_2CO_2CH_3$, the methyl ester may be hydrolyzed, and the acid may be reacted with p-nitrophenol in the presence of dicyclohexyl-carbodiimide to produce

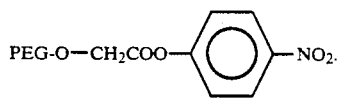

This polymer is, following purification, in turn reacted with available free amino group(s) of the CSF-1.

In another embodiment PEG-OH is reacted with a chloroformate (also called a chlorocarbonate) to form a PEG active ester also called (PEG-PNP). After the PEG active ester is formed, it is reacted with CSF-1 to form a PEG/CSF-1 conjugate. See also Veronese, et al., 1985, *Biochem and Biotech.*, 11:141–152 which is hereby incorporated by reference in its entirety. Chloroformates may be purchased from companies such as Aldrich. They may also be made as shown in equation (1).

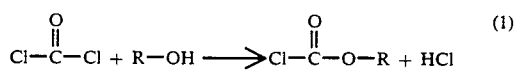

The chloroformate is made by reaching phosgene also known as carbonyl chloride with an alcohol (R-OH) which contains electron withdrawing substituents on the carbon that carries the —OH. The alcohol is preferably an acidic alcohol, more preferably an acidic alcohol which contains aromatic rings which have high extinction coefficients. Examples of R groups are: N-hydroxy-succinimide, N-hydroxy-sulfosuccinimides, cyanomethyl esters, all nitro, chloro, and cyano substitutions on benzene, naphthalene, or larger aromatic ring systems which may or may not contain hetero-atoms, such as pyridine, para-nitrophenol (PNP), ortho-nitrophenol (ONP), etc. Most preferred R groups are PNP and ONP.

After the chloroformate is formed, it is reacted with PEG-OH to form a PEG active ester as shown in equation (2).

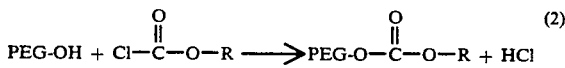

The chloroformate is reactive at two sites; at the bond between the chlorine and carbonyl group (more reactive) and the bond between the carbonyl and O-R group (less reactive). The more reactive site is where the chloroformate binds to the PEG. PEG-OH and the chloroformate are preferably added together at room temperature in an appropriate solvent, such as $CHCl_3$, or $CH_2Cl_2$. Preferably an acylation catalyst is added between 0 and 1 hours later, preferably the catalyst is pyridine or dimethyl pyridine. Preferably, the chloroformate is added up to 12M excess, more preferably to a 2M excess. The mixture is allowed to mix for preferably 4 hours, more preferably 16 hours. At this point, a precipitate may form. It is removed by filtration and discarded. Filtering devices such as Whatman glass fiber filters (GH/B) are acceptable. The resulting solution contains the PEG active ester as well as unreacted PEG and excess chloroformate. It is precipitated by adding an ether, preferably the ether is diethyl ether. The precipitate contains the PEG active ester and can be washed with appropriate solvents such as ether, redissolved and reprecipitated if necessary.

After the PEG active ester is formed, it is conjugated with CSF-1 as shown in equation (3):

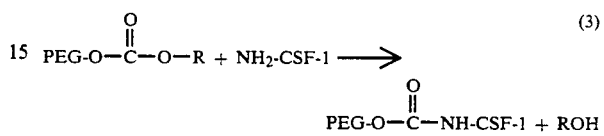

The chloroformate portion of the PEG active ester still has the less reactive site available. At this site, the covalent bond between the PEG and CSF-1 is formed. In the final product, the PEG moiety is bound to CSF-1 by a urethane, also called a carbamate, linkage having the structure

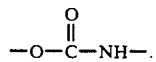

This linkage is relatively stable and will keep PEG conjugated to CSF-1 with little or no hydrolysis under physiological conditions.

Homodimeric recombinant CSF-1 from *E. coli* does not contain significant numbers of reactive free sulfhydryl groups after refolding has correctly proceeded to completion. The clone could be modified genetically, however, to include one or more novel cysteine residues that might retain sulfhydryl groups following refolding. The CSF-1 mutein so produced must still retain significant biological activity to be useful herein.

Alternatively, free sulfhydryls can be generated by creation of selected heterodimers or by partial refolding of homodimers such that certain SH groups, such as on $cys_{159}$, are available for modification by activated polymers.

If the protein is being conjugated via a cysteine residue, a preferred mode of conjugation is as follows: $mPEG-NH_2$ as described above is reacted at room temperature for preferably 0.5–1.5 hours with N-maleimido-6-aminocaproic ester of 4-hydroxy-3-nitrobenzene sulfonic acid (mal-sac-HNSA), which is described by Nitecki et al., *High-Technology Route to Virus Vaccines* (Amer. Soc. for Microbiol., 1985), pp. 43–46, mentioned supra. The latter reaction is preferably conducted with about a 5-fold molar excess of mal-sac HNSA over $PEG-NH_2$. After removal of hydrolysed or unreacted mal-sac HNSA (e.g., by dialysis, diafiltration, or size-exclusion chromatography), the reagent can then be reacted with the protein at room temperature in a buffer using equimolar amounts of reagent and protein. Other reagents, such as N-succinimidyl-4-(N-maleimidomethyl)-cyclohexane-1-carboxylate (SMCC), or $XCH_2CO-NH(CH_2)_5$-HNSA ester wherein X is Br, Cl, or I, can perform the same function as mal-sac HNSA under a variety of reaction conditions known to those skilled in the art.

Purification of Conjugates

After the conjugation reaction, a mixture of species, the identity of which will depend upon the reaction conditions, are likely present. These species which differ in the number of PEG moieties conjugated to CSF-1 may be separated by various methods including chromatography, electrophoresis and salt fractionation. Hydrophobic interaction chromatography (HIC) using phenyl-Sepharose has been shown to be particularly useful. Size separation may also be accomplished using non-reducing SDS-PAGE or molecular sieve chromatography. In addition, salting out of CSF-1 conjugates as well as conjugates of other proteins such as interleukin-2 (IL-2) has also been shown to be useful. Commonly used salts are ammonium sulfate, $(NH_4)_2SO_4$; sodium sulfate, $Na_2SO_4$; magnesium salts and phosphates. The more highly conjugated species precipitated at lower salt concentrations than did less conjugated and unconjugated protein. Recycling of partially purified species through any of these techniques may result in a substantially homogeneous species of conjugated protein with regard to the number of polymers per molecule of protein.

Formulations

The protein thus modified and optionally purified as to extent of conjugation is then formulated in a non-toxic, stable, pharmaceutically acceptable aqueous carrier medium, preferably at a pH of about 3 to 8, more preferably 5-8. Administration is by conventional protocols and regimens, preferably systemic, including intravenous administration. For in vitro applications, as for diagnostic purposes, the modes of administration and formulation are not critical. Aqueous formulations compatible with the culture or perfusion medium will generally be used. When used in vivo for therapy, the composition may include conventional physiologically acceptable excipients, such as water for injection, buffers, and stabilizers, as are known in the art. A water-soluble carrier such as mannitol may optionally be added to the medium.

Modified CSF-1 may be used either as the sole active ingredient or in combination with other proteins or compounds having complementary activity. Such other compounds may include antitumor agents such as adriamycin of lymphokines such as IL-1, -2, -3, -4, interferons (alpha, beta or gamma), GM-CSF; G-CSF, and tumor necrosis factor. The effect of the modified CSF-1 may be improved by the presence of such additional components. A summary of formulation techniques for pharmaceutical compositions, including protein, is found, for example, in *Remington's Pharmaceutical Sciences*, Mack Publishing Co., Easton, Pa., latest edition.

The dosage level of protein in the formulation will depend on the in vivo efficacy data obtained after preclinical testing and may vary depending upon the clinical application. The medium in which the protein is dissolved will be at a pharmaceutically acceptable pH when the mixture is reconstituted.

If the formulation is lyophilized, the lyophilized mixture may be reconstituted by injecting into the vial a conventional parenteral aqueous solvent such as, e.g., distilled water for injection.

The reconstituted formulation prepared as described above is suitable for parenteral administration to humans or other mammals in therapeutically effective amounts (i.e., amounts that eliminate or reduce the patient's pathological condition without mortality or unacceptable morbidity) to provide therapy thereto. CSF-1 therapy may be appropriate for a variety of indications such as enhancing the immune system, enhancing cytotoxicity of macrophages, increasing monocytic and granulocytic white blood cell count, treating infectious diseases such as cytomegalovirus and bacterial infections (e.g., Gram-negative sepsis) by therapeutic or prophylactic administration to mammals, treating tumor burden such as sarcoma or melanoma in mammals, treating cholesterolemia (as described for GM-CSF by Nimer et al (1988) JAMA 260:3297-3300) and/or healing wounds in mammals. In addition, CSF-1 may be combined with G-CSF for stimulation of the immune system, as described in European Patent Publication No. 0273778 published Jul. 6, 1988, the disclosure of which is incorporated herein by reference.

The dose and dosage regimen of the conjugated CSF-1 will depend, for example, upon the pharmacokinetics of the drug, the nature of the disease or condition, the type and length of polymer, the characteristics of the particular CSF-1, e.g., its therapeutic index, its spectrum of activities, the patient, and the patient's medical history. Different modified CSF-1 proteins are expected to have different pharmacokinetic and therapeutic properties that are advantageous for different routes of administration. A long-acting drug might only be administered every 3-4 days, every week, or once every two weeks. The clearance rate can be varied to give ultimate flexibility to fit the particular need of the patient by changing, e.g., the type of polymer, the size of the polymer attached, and the amino acid sequence to which the polymer is attached.

In the following examples, which illustrate the invention further, all parts and percentages are by weight unless otherwise noted, and all temperatures are in degrees Celsius.

EXAMPLE I

Preparation of PEGylated CSF-1 Via Linkage Method One

A. Preparation of Activated PEG-NHS

A linear ester of monomethyl PEG of average molecular weight 7000 can be obtained by first reacting monomethyl PEG-7000, which is available from Union Carbide, with glutaric anhydride at 100° to 110° C. for four hours or by a method similar to that of Abuchowski et al., *Cancer Biochem. Biophys.*, 7:175-186 (1984), the disclosure of which is incorporated herein by reference. The resulting PEG-glutarate was reacted with N-hydroxysuccinimide in the presence of dicyclohexylcarbodiimide, as described in detail by Abuchowski et al., supra, on page 176. The resulting product is methoxypolyethylene glycolyl N-succinimidyl glutarate, hereinafter designated as PEG*-7000. Reaction of PEG-4800 Carbide) by the same method resulted in PEG*-4800.

A PEG-11,000 glutaramido NHS species (PEG"-11,000) was prepared as follows, according to the procedure of Rajasekharam Pillai et al., *J. Org. Chem.* 45:5364-5370 (1980): A linear monomethyl PEG of average molecular weight 11,000 daltons obtained from Union Carbide (1.5 mmole) was first dissolved in 10 ml methylene chloride and then 1.8 ml (22.2 mmole) of pyridine and 6.0 g (31.6 mmole) p-toluene-sulfonyl chloride were added. The flask was flushed with nitrogen and the reaction mixture stirred at room temperature overnight. The mixture was concentrated to about 5 ml and the product precipitated with 75 ml ethyl ether. The precipitate was collected and washed with ether. The product (mPEG-tosylate) was recrystallized from ethanol.

The mPEG-tosylate (about 1.5 mmole) was dissolved in 20 ml dimethylformamide, and 2.5 g (17.0 mmole) potassium phthalimide was added. The solution was heated at reflux under nitrogen for four hours. The precipitate that formed was filtered off and the filtrate was added dropwise to 300 ml ether to precipitate the product. The precipitate was filtered and washed with ether. The product was suspended in 30 ml methylene chloride and stirred for 0.5 hours. Insoluble impurities were filtered off and the product (mPEG-phthalimide) was precipitated with ether. Next, the mPEG-phthalimide (about 1.1 mmole) was dissolved in 15 ml ethanol and 2.0 ml (41.2 mmole) hydrazine hydrate was added. The mixture was refluxed overnight. The reaction mixture was cooled to room temperature and the product was precipitated with ether.

The precipitate was collected by filtration and resuspended in 25 ml methylene chloride. Insoluble impurities were filtered off and the product was precipitated with ether. This precipitate, mPEG-11,000-amine, was suspended in $CH_2Cl_2$, filtered, and precipitated with ether two more times. The second time it was completely soluble in methylene chloride.

A total of 0.5 g of the mPEG-11,000-amine was dissolved in 10 ml dioxane to which was added 0.25 g glutaric anhydride. The reaction was carried out for four hours at room temperature. After the reaction, the product, mPEG-NHCO(CH$_2$)$_3$COOH, was precipitated with about 100 ml ether. The mixture was filtered, and the product was redissolved in $CH_2Cl_2$, filtered into ether, filtered and dried. The yield of product was 200 mg.

The mPEG-NHCO(CH$_2$)$_3$COOH was then reacted with N-hydroxysuccinimide in the presence of dicyclohexylcarbodiimide, as described above for preparing PEG*-7000. The resulting product is designated herein as PEG"-11,000.

B. Purification and Refolding of CSF-1

An *E. coli* strain HW22, transformed with the plasmid pJN653 containing the SCSF/N∇3C∇158 gene (the plasmid being deposited as ATCC No. 67,561 on Nov. 12, 1987) was grown in a 10-liter fermenter in basal medium containing 96 mM (NH$_4$)$_2$SO$_4$, 28 mM KH$_2$PO$_4$, 4 mM Na$_3$ citrate.2H$_2$O, 1.7 ml/l TK9 (30 mM ZnSO$_4$, 30 mM MgSO$_4$, 1 mM CuSO$_4$), with sterile additions of 6.5 g/l glucose, 2.2 mM MgSO$_4$.7H$_2$O, 95 μM, FeSO$_4$.7H$_2$O, and 26 mg/l thiamine.HCl at 30° C. until an OD$_{680\ nm}$ of 10 was reached. Casamino acids were then added to 2% w/v. CSF-1 expression was induced by shifting the temperature of the culture to 37° C. After four hours the absorbance at 680 nm reached 79.

The cells were harvested by 5-fold concentration and diafiltered against ten volumes of 5 mM EDTA, pH 8.5, using Dorr-Oliver tangential cross-flow microporous filtration. The cells were disrupted by three passes at 7,500 psi in a Manton-Gaulin high pressure mechanical cell homogenizer. 1-Octanol was added to 0.1% (v/v) and the homogenate was held overnight at 4° C.

The homogenate was made 25% sucrose by addition of a 63% w/v sucrose solution. The insoluble protein fraction (refractile bodies) was separated from cell debris by continuous flow disk stack centrifugation (Westphalia SB7) at 9000 × g, 1 liter/minute and 4°–6° C. The wet pellet was mixed 50:50 (w/v) with deionized water and stored at −20° C. in aliquots.

Twenty-five grams of refractile body suspension (approximately 390 mg of protein) were solubilized in 250 ml of 8M urea containing 25 mM Tris, 10 mM sodium phosphate buffer (pH 8.4), 1 mM ethylenediamine tetraacetic acid (EDTA), and 4 mM dithiothreitol (DTT). After two hours at room temperature, the solution was clarified by centrifugation at 15,000 × g for 15 minutes. A 150-ml aliquot of the solubilized CSF-1 was then loaded onto a 5 × 8 cm DEAE-Sepharose (Pharmacia) column equilibrated in 6M urea containing 25 mM Tris, 10 mM sodium phosphate buffer (pH 7.0). The column was washed with 1 bed volume of the above solution, which had been modified to contain 1 mM DTT and 1 mM EDTA, and the CSF-1 was then eluted with a 1.4-liter salt gradient of 0–0.6M sodium chloride in the wash buffer. The CSF-1 peak eluted at approximately 0.06M sodium chloride.

The remaining 90 ml of solubilized refractile bodies was then purified over the DEAE-Sepharose column in identical fashion. The combined CSF-1 pools (165 ml) contained approximately 250 mg of protein at a purity of approximately 50%.

The CSF-1 was then refolded by diluting the DEAE-pool into refolding buffer containing 50 mM Tris (pH 8.5), 5 mM EDTA, 2 mM reduced glutathione, 1 mM oxidized glutathione, pre-cooled to 4° C. The CSF-1 was allowed to refold for 30 hours at 4° C. The pH of the refolded CSF-1 was then adjusted to 6.8 using 8.5% phosphoric acid solution. The solution was then clarified by centrifugation for 10 minutes at 15,000 × g and loaded onto a 5 × 4 cm DEAE Sepharose column pre-equilibrated in 10 mM sodium phosphate, 25 mM Tris (pH 6.8). The column was washed with 300 ml of this buffer and then eluted with a 700 ml, 0–0.6M sodium chloride gradient in the same buffer system. The CSF-1 eluted at approximately 120 mM sodium chloride. Ammonium sulfate (4M stock pH 7.0) was then added to the 95-ml DEAE pool to a final concentration of 1M. The CSF-1 was then filtered through a Nalgene 0.45 micron filter and loaded (at 4° C.) onto a 21.5 × 150 mm Bio-Rad TSK Phenyl-5-PW column equilibrated in depyrogenated 1.5M ammonium sulfate, 0.1M sodium phosphate (pH 7.0). The column was washed with two bed volumes of this loading buffer and then eluted in 0.1M sodium phosphate (pH 7.0) using a 45-minute gradient in which the ammonium sulfate concentration decreased from 1.5M to 0M and the ethylene glycol concentration increased from 0–60% (v/v). All operations were carried out at 4° C. under essentially pyrogen-free conditions. The CSF-1 eluted at approximately 0.6M ammonium sulfate in 30% ethylene glycol. The CSF-1 was then extensively dialyzed into 10 mM Hepes buffer (pH 7.5) containing 150 mM sodium chloride and subsequently was filter sterilized through a Millex 0.45 micron filter.

Approximately 50 mg of purified SCSF/N∇3C∇158 CSF-1 was obtained. Greater than 90% of the final CSF-1 product migrated as a single species on SDS-PAGE, and the same product was approximately 96% one species as analyzed by RP-HPLC in acetonitrile/TFA. The specific activity was about $1.5$–$1.7 \times 10^8$ units/mg (units determined as colony forming units equivalents using a CSF-1-dependent cell line, and protein concentration determined using A$_{280}$ nm and an extinction coefficient of 0.6, estimated from amino acid composition determinations). This specific activity is at least equivalent to, if not greater than, that of purified native Mia PaCa CSF-1. The endotoxin content of the refolded, purified CSF-1 product, determined by LAL assay, was 0.5–1 ng/mg of CSF-1.

In a similar manner, E. coli protein produced under control of the $P_L$ promoter from DNA encoding SCSF/N∇2C∇150 as described in European Patent Publication No. 0272779 was refolded and purified in a similar manner. The vector used to transform the E. coli was prepared by substituting the appropriate synthetic fragment for the excised HindIII/BstXI DNA of the appropriate CSF-17 vector to encode the CSF/N∇2, lacking N-terminal glu-glu.

C. Conjugation of PEG*-7000 to CSF-1

The CSF-1 protein (SCSF/N∇2C∇150) in Section B was dialyzed (1 mg protein/ml) into a medium of 10 mM Hepes buffer, pH 7.2 containing 100 mM NaCl. The PEG*-7000 was dissolved rapidly in a small volume of water and immediately added to the protein solution, which was continuously stirred throughout the reaction. A 3-fold to 30-fold molar excess of PEG*-7000 over CSF-1 dimer was employed. Reaction was complete in about 30 minutes at 20° C. and in about three hours at 4° C.

Figure 3B:
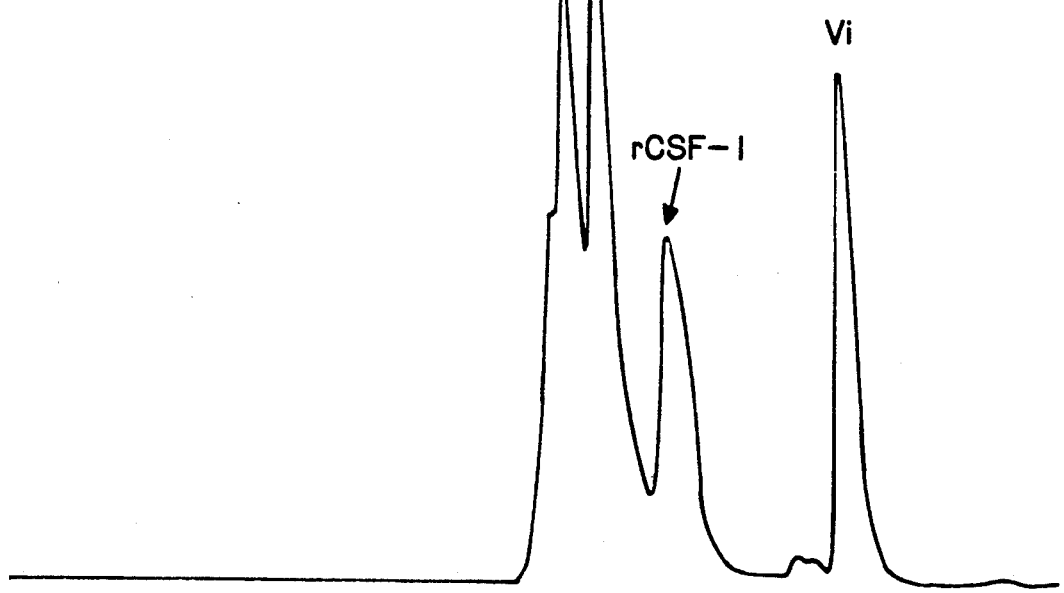
FIG. 3B shows the HPLC chromatogram of the same rCSF-1 derivatized with PEG-NHS of 7000 dalton average molecular weight.

The samples were analyzed by size exclusion HPLC. FIG. 3A shows the chromatogram of underivatized rCSF-1 (SCSF/N∇2C∇150) sample prior to the experiment. FIG. 3B shows the chromatogram of 100 μg of the same CSF-1 sample after derivatization with a 5-fold molar excess of PEG*-7000 for 30 minutes at 20° C. Radioimmunoassay, performed according to the method of Stanley, R. and Guilbert, J. Imm. Methods, 42:253–284 (1981), confirmed that the first three major absorbance peaks observed in FIG. 3B contained rCSF-1. See Table I.

The fractions 30, 32, 34, 36, 37, 38, 39, 41 and 42 were also analyzed for biological activity, using the mouse bone marrow assay described by Moore et al., J. Immunol. (1983) 131:2397 and by Prystowsky et al., Am. J. Pathol. (1984) 114:149, the disclosures of which references are incorporated herein by reference. Table I provides the results.

TABLE I

| | Derivatization with PEG*-7000 Clone: SCSF/N∇2C∇150 | | |
|---|---|---|---|
| Fraction #[a] | Bone Marrow[1] | RIA[1] | Bioactivity Ratio[2] |
| 30 | 0 | 215,000 | 0 |
| 32 | 51,900 | 288,000 | 0.18 |
| 34 | 175,100 | 576,000 | 0.30 |
| 36 | 210,700 | 454,000 | 0.46 |
| 37 | 522,000 | 886,000 | 0.59 |
| 38 | 809,300 | 445,000 | 1.82 |
| 39 | 660,000 | 348,000 | 1.90 |
| 41 | 1,281,000 | 800,000 | 1.60 |
| 42 | 1,048,000 | >1,000,000 | ND |

[a]Fractions were assayed after dilution to about 1000 RIA U/ml.
[1]Units/ml
[2]Bioactivity ratio = bioassay divided by RIA
ND = Not determined The results in Table I and those below show that the unreacted rCSF-1 and the smallest molecular weight peak of derivatized rCSF-1 retained approximately full bioactivity (within experimental error). Larger species retained much less residual bioactivity. The reaction with PEG*-7000 apparently did not significantly affect the radioimmunoassay (RIA) reactivity of CSF-1, because the unfractionated, derivatized rCSF-1 retained approximately full RIA immunoreactivity per mg of protein.

D. Conjugation of PEG"-11,000 to CSF-1

Biologically active protein was purified and refolded after expression of a construct encoding SCSF/C∇150 in E. coli under control of the $P_L$ promoter in a vector constructed as described in European Patent Publication No. 0272779 published Jun. 29, 1988. The strain used was an E. coli λ lysogen, DG116, transformed with the plasmid O/E $pP_L$ CSF-17 asp$_{59}$/C∇150 (ATCC No. 67,389). The protein was produced intracellularly in a monomeric, insoluble form, and purified and refolded as described in PCT Publication No. WO 88/08003 supra.

A total of 2 mg of this purified CSF-1 at 1 mg/ml protein was dialyzed into Hepes buffer at pH 7.2 containing 100 mM NaCl. The PEG"-11,000 was dissolved rapidly in a small volume of water and immediately added to the protein solution, which was continuously stirred throughout the reaction. An 8-fold molar excess of PEG"-11,000 over CSF-1 dimer was employed. Reaction was completed in 30 minutes at 20° C. This CSF-1 reacted with the PEG"-11,000 in a fashion very similar to the reaction of SCSF/N∇2C∇150 with the PEG*-7000. As Table II shows, mild PEGylation (1–2 per dimer) again had minimal effect upon bioactivity, while the highly modified pool had significantly reduced activity.

TABLE II

| | Comparison of Derivatization of rCSF-1 With PEG"-11,000 and PEG*-7000 | |
|---|---|---|
| Extent of PEGylation[1] | PEG*7000 % Bioactive (Compared to Underivatized SCSF/N∇2C∇150) | PEG"-11,000 % Bioactive (Compared to Underivatized SCSF/C∇150) |
| Multiple | 0–20 | 8–11 |
| 1 to 2 per CSF-1 dimer | 100 | 90–100 |

[1]Estimated from apparent native molecular weight as measured by SEC-HPLC and SDS-PAGE.

Figure 4:
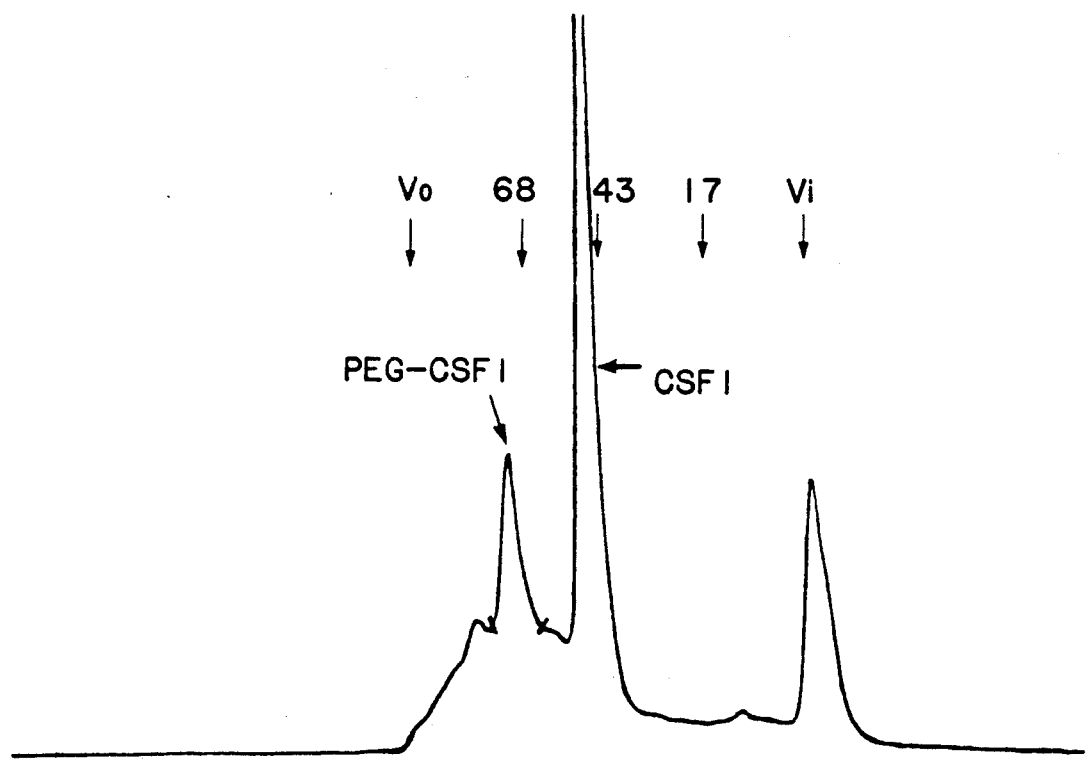
FIG. 4 shows a size exclusion HPLC chromatogram of rCSF-1 (SCSF/C∇150) derivatized with PEG-NHS of 11,000 daltons average molecular weight.
Figure 8:
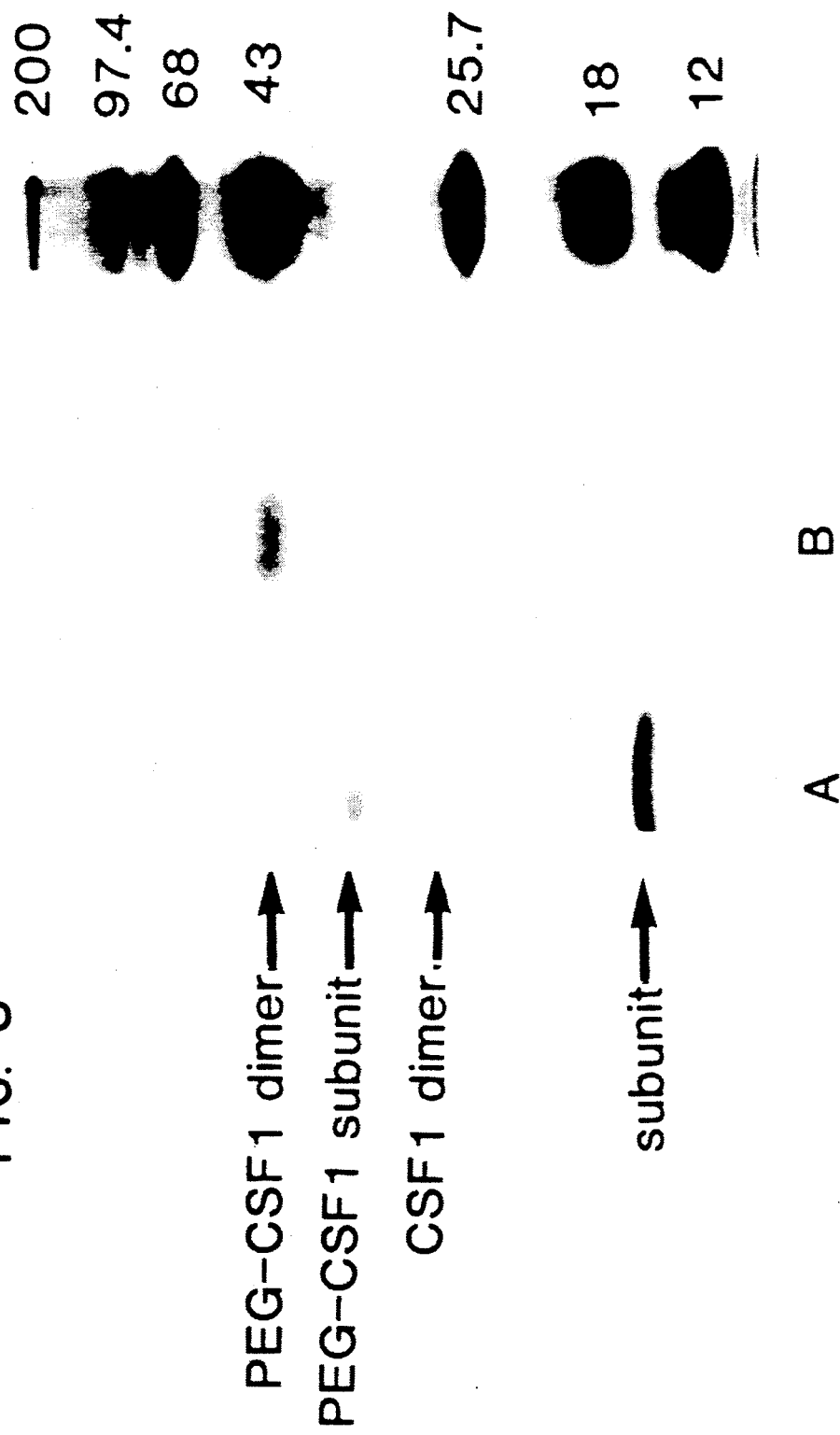
FIG. 8 shows SDS-PAGE analysis of rCSF-1 derivatized with PEG-11,000 (SCSF/C∇150). Gel (10%), stained for protein with Coomassie blue, is of the sample used in FIG. 5, with and without reduction of disulfide bonds.

FIG. 4 shows a size exclusion HPLC chromatogram of 8 mg of rCSF-1 (SCSF/C∇150) derivatized with PEG"-11,000. The mildly derivatized fraction, pooled as shown in the figure, was found to retain essentially full biological activity, and to migrate with an apparent molecular weight of 80,000 daltons on sizing, and 45,000 daltons on nonreduced SDS-PAGE (FIG. 8). This fraction was recovered at an overall yield of about 20%.

The difference in sizes of PEG-CSF estimated by these two techniques is consistent with observations made by others. PEG can alter the ability of a protein to bind SDS, affecting mobility on SDS-PAGE; and it can also affect size exclusion estimations, e.g., by hydrophobic interaction with the column matrix.

The endotoxin level of this sample, as assayed by the Limulus amebocyte lysate (LAL) assay, was found to be less than 1 ng/absorbance unit at 280 nm ($A_{280}$ unit) protein. (LAL assay is described by a product brochure (1982) for Pyrotell brand of LAL available from Associates of Cape Cod, Inc., Woods Hole, MA; it is also described by Watson et al. (eds.) "Endotoxins and Their Detection with the Limulus Amebocyte Lysate Test", *Proceedings of an International Conference on Endotoxin Standards and Limulus Amebocyte Lysate Use with Parenteral Drugs*. Alan R. Liss, Inc., New York (1982); and by Levin et al. (1964) *Bull, Johns. Hopkins Hosp.,* 115:265.)

E. Conjugating of PEG*-4800 to CSF-1

The same conditions used for PEG"-11,000 were used to react the rCSF-1 from the clone SCSF/C∇150 with PEG*-4800. The CSF-1 was successfully derivatized, and the pool that was mildly derivatized (at one or two sites) retained essentially full bioactivity.

F. Pharmacokinetics of PEGylated CSF-1 and Unmodified CSF-1 in Rats

Three male CD rats (Charles River Breeding Labs, Wilmington, MA) of average weight 161 g were injected in the tail vein with 1 mg/kg of the mildly derivatized fraction of PEG"-11,000-derivatized CSF-1 from the SCSF/C∇150 clone described above and shown in FIG. 8. Blood plasma samples were collected by an indwelling catheter, and CSF-1 titer was determined by RIA. Urine samples were collected at 0, 30, and 120 minutes and assayed. Additional data were also collected using the underivatized rCSF-1 and rCSF-1 expressed in mammalian cells (COS) that arises from a glycosylated 522-amino acid precursor (LCSF). The rats in the experiments with unmodified CSF-1 had an average weight of 178 g and were injected with 125 $\mu$g/kg of the unmodified CSF-1. All other conditions were the same.

Figure 5:
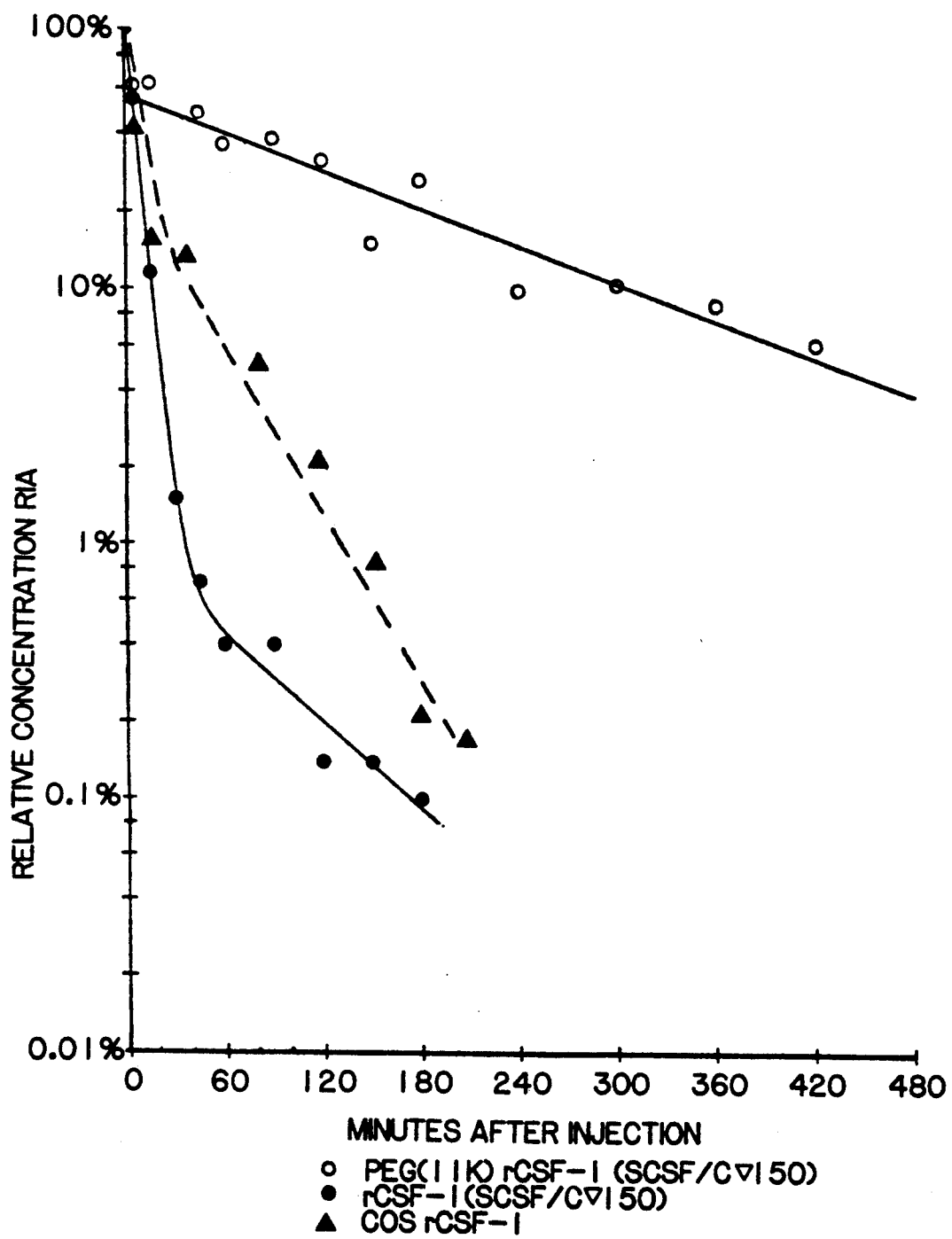
FIG. 5 shows a graph of CSF-1 concentration in rat blood plasma versus time for E. coli rCSF-1 (SCSF/C∇150), the dimeric product derived from the rCSF-1 with the sequence in FIG. 2 [lacking the leader sequence and a C-terminal sequence, but retaining essentially all of the N-terminal methionine present in the E. coli construct], rCSF-1 expressed in mammalian cells (COS) that arises from a glycosylated 522-amino acid precursor (LCSF) and PEG-11,000-derivatized E. coli rCSF-1 (SCSF/C∇150).

FIG. 5 compares the time courses of blood clearance of modified and unmodified CSF-1 protein. The systemic clearance is calculated by dividing the dose by the area under the blood plasma curve. The data show that the systemic clearance of derivatized rCSF-1 in the blood is 0.302 ml/min/kg versus 3.84 ml/min/kg for underivatized rCSF-1. This represents a 12.7-fold extended residence time of the derivatized as compared to the underivatized protein.

Figure 6:
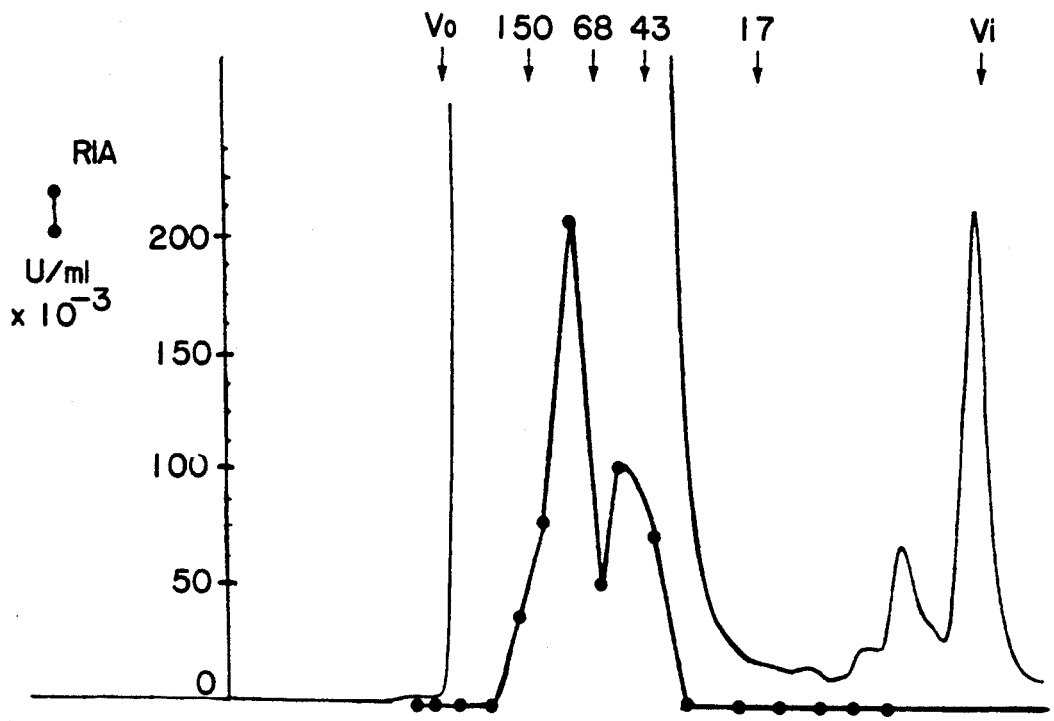
FIG. 6 shows a size exclusion HPLC chromatogram of rat blood plasma 120 minutes after intravenous injection of PEG-11,000-derivatized rCSF-1 (SCSF/C∇150). Radioimmunoassay (RIA) and absorbance at 280 nm are plotted.

FIG. 6 shows size exclusion HPLC of the rat blood plasma 120 minutes after injection of the derivatized CSF-1 (SCSF/C∇150). This figure shows that the RIA-detectable rCSF-1 signal in the blood plasma was 43–80 Kd in apparent size two hours after intravenous injection. This observation suggests that the RIA signal that was measured in the pharmacokinetic experiment (at 120 min.) represents intact PEG-rCSF-1 and rCSF-1. Western blotting by the technique of Burnette, (1981) *Anal. Biochem.* 112:195–203 (developed with an antiserum to recombinant CSF-1 capable of detecting CSF-1 fragments, followed by $^{125}$I-protein A) of a non-reduced SDS-PAGE gel of urine and plasma verified that the rCSF-1 antigen detected by Western blotting was apparently intact, dimeric, and the same size as the material that was injected.

EXAMPLE II

Preparation of Activated PEGylated CSF-1 Via A Second Linkage Method

A. Preparation of PEG-Ester

1. The carboxymethyl derivative of mPEG-5000 was prepared:

Sodium-naphthalene was prepared by addition of 0.15 g Na to a solution of 0.64 g naphthalene in about 20 ml tetrahydrofuran (THF) freshly distilled from sodium benzophenone. Monomethylpoly(ethylene glycol) of average molecular weight of 5000 ("mPEG 5000") was dried overnight in a vacuum dessicator with $P_2O_5$. The Na-napthalene solution was added dropwise to a solution of 2.5 g mPEG 5000 in ~50 ml dry THF (freshly distilled). When the green color persisted in the solution to indicate excess, base addition was ceased and 1.2 ml $BrCH_2COOCH_3$ was added dropwise. The green disappeared and the mixture became cloudy. The mixture was stirred overnight at room temperature. The cloudy mixture was poured into a flask containing about 70 ml cold ether. The precipitate was collected by vacuum filtration and washed with ether. The dry solid was dissolved in 75 ml 1M NaOH and stirred at room temperature for 2.5 hours to hydrolyze the methyl ester. The pH was adjusted to about 3 by addition of HCl and the solution concentrated on a rotary evaporator. The residue was taken up in $CH_2Cl_2$ and stirred for about one hour. Insoluble material was filtered off and the solution was poured into ether. The solid was collected by vacuum filtration, washed with ether, and dried in a vacuum dessicator over $P_2O_5$. This yielded the desired carboxymethyl mPEG-5000 acid. The acid was titrated to demonstrate that complete conversion had taken place. The preparation of carboxymethyl mPEG-5000 was repeated at a larger scale. The precipitate was collected and dried. Yield 8.5 g. Titration showed about 102% acid. The reference for this experiment is Buckmann et al., *Makromol. Chem.* 182:1379 (1981).

2. Para-nitrophenyl ester of carboxymethyl mPEG-5000 was prepared:

A total of 1 g mPEG-5000 acid ($2\times10^{-4}$ moles) was dissolved in 3 ml $CHCl_3$. To this solution was added 0.28 g p-nitrophenol ($2\times10^{-4}$ moles). The solution became pale yellow. Then 0.041 g of dicyclohexyl carbodiimide (DCC) ($2\times10^{-4}$ moles) was dissolved in a small amount of $CHCl_3$ and added dropwise to the PEG-acid solution at room temperature. After about 10 minutes of stirring, 2 $\mu$l of the $CHCl_3$ mixture was added to 1.0 ml 0.01M phosphate buffer, pH 7.0. The absorbance at 400 nm of the p-nitrophenol anion was 0.2443. 5N NaOH was added, increasing the $A_{400}$ to 0.5847 (% ester is 58.2% as calculated by the formula below:

$$\% \text{ ester} = \frac{A_{400} \text{ after NaOH} - A_{400} \text{ before NaOH}}{A_{400} \text{ after NaOH}} \times 100)$$

After about three hours of reaction 1 $\mu$l of the $CHCl_3$ mixture was added to 1.0 ml of 0.01M phosphate, pH 7.0. The $A_{400}$ was 0.2238. When 50 $\mu$l 5N NaOH was added, the $A_{400}$ was 1.154, yielding 80.6% ester.

A precipitate, dicyclohexylurea, appeared and was filtered off through a glass fiber filter and washed with $CHCl_3$. The ester was precipitated by adding about 300 ml anhydrous ethyl ether. The mixture was allowed to precipitate for about three hours and was then filtered through a glass frit. The precipitate was then redissolved in CHCl$_3$, reprecipitated with about 100 ml ethyl ether, and filtered through a medium glass frit. A small amount of damp solid was dissolved in 0.01M phosphate buffer, pH 7.0. The A$_{400}$ was 0.0240; when 50 μl 5N NaOH was added, the A$_{400}$ increased to 3.330 (% ester was 99.3).

The main precipitate was dried in a vacuum desiccator overnight. The flask in which it was contained was washed with water and the residues were lyophilized. A total of 4 mg of the precipitate was then dissolved in 2 ml 0.01M phosphate at pH 7.0 (A$_{400}$=0.0276). When 50 μl 5N NaOH was added, the A$_{400}$ was 3.50 (off-scale). A total of 200 μl of the solution was diluted to 800 μl 0.01M phosphate, pH 7.0. The A$_{400}$ was 0.7985. Calculated % ester=99.3.

A total of 1.5 mg of lyophilized residues was dissolved in 1.0 ml of 0.01M phosphate, pH 7.0. The absorbance was 0.0680. A total of 50 μl of 5N NaOH was added and the A$_{400}$ was 1.106 (% ester-93.9). The residues on the filter from the main precipitate were washed with water and lyophilized over a weekend. The weight was 131 mg of fluffy white powder. A small amount was dissolved in 0.01M phosphate, pH 7, and the A$_{400}$ was 0.0859. On adding 50 μl 5N NaOH, the A$_{400}$ was 0.6794 (87.4% ester).

Structure of ester:

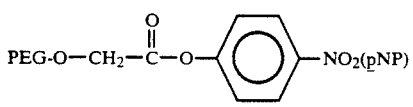

B. PEGylation of CSF-1 (asp$_{59}$SCSF/C∇150)

The para-nitrophenyl ester just described was coupled with the asp$_{59}$SCSF/C∇150 refolded protein described in Example I as follows:

The rCSF-1 (200 μg at 1 mg/ml) was dialyzed into 20 mM Hepes buffer, pH 7.2, containing 100 mM NaCl. A total of 0.8 mg of the para-nitrophenyl ester was dissolved in a small volume of water and 259 μg of this solution was immediately added to the SCSF/C∇150. The conjugation was carried out at 20° C. for four hours, and the samples were analyzed by size exclusion HPLC. The mildly derivatized rCSF-1 (corresponding to about 1 or 2 PEG molecules per CSF-1) retained essentially full bioactivity as assayed on mouse bone marrow.

If the reaction is carried out in cuvettes in a dual-beam Hewlett-Packard spectrophotometer, release of para-nitrophenol anion can be monitored, permitting the coupling reaction to be stopped reproducibly after a given amount of release has occurred.

EXAMPLE III

Preparation of PEGylated CSF-1 Via a Third Linkage Method

A. Preparation of Activated PEG-Ester (PEG-PNP)

25 grams (2.5 mmole) of monomethyl PEG of average molecular weight of 10000 (m-PEG 10,000; Union Carbide) containing only low concentrations of diol was dissolved in 250 ml CH$_2$Cl$_2$ in a 500 ml 3 neck round bottom flask. 5 grams (25 mmoles) p-nitrophenyl chloroformate (PNP-chloroformate) and 3 grams (25 mmole) dimethylaminopyridine (DMAP) were added. The mixture was stirred overnight under nitrogen at room temperature. The reaction mixture was filtered to remove DMAP.HCl and concentrated to 100 ml. The concentrated solution was added to 1 liter ether with stirring. The precipitate was collected on a coarse scintered glass filter. The precipitate was then stirred with about 400 ml methylene chloride for approximately 1 hour and then filtered and concentrated to about 100 ml. The PEG ester was precipitated again by addition of the solution to 1 liter ether. The precipitate was collected using a glass fiber filter and dried in a vacuum dessicator. The yield was 17.5 grams.

The product was assayed for p-nitrophenyl carbonate content. 10.3 mg (1.03×10$^{-6}$ mole) was dissolved in 10 ml 0.1M sodium phosphate, pH8. Free or unreacted p-nitrophenyl (PNP) impurity was determined by absorbance at 400 nm. The initial A$_{400}$ was 0.37. Addition of 50 microliters of 5N NaOH to 1.0 ml PEG-PNP hydrolyzed all ester present and A$_{400}$ was 2.06. If all the product weighed (10.3 mg) had been PEG-PNP, (i.e. no free PNP was present) 1.03×10$^{-4}$ mole/liter PNP would have been released having an A$_{400}$=1.85 which is referred to as the theoretical maximum A$_{400}$. Therefore $$\frac{2.06 - 0.37}{1.85} \times 100 = 91\%$$

of the material weighed was actually PEG-PNP. Since the initial absorbance (0.37) was rather high, free PNP was apparently present. The product was further purified by dissolving in about 75 ml CH$_2$Cl$_2$ and re-precipitating by addition to 1.2 liters ether. The precipitate was collected, dried (15.8 grams) and reassayed.

$$\frac{A_{400} \text{ after NaOH} - A_{400} \text{ before NaOH}}{\text{theoretical maximum } A_{400}} \times 100 =$$

$$\frac{1.78 - 0.157}{1.82} \times 100 = 89\%$$

B. Preparation of PEGylated CSF-1 (SCSF/N∇C∇158)

CSF-1 was produced essentially as described in Example I. CSF-1 was concentrated to about 10 mg/ml in 0.05M Na borate, pH 9.0. 5 mg PEG-PNP obtained as a solid from Example III Part A was added per ml of CSF-1. (approximately a 1:1M ratio). The reaction was continued for 2 hrs at room temperature.

NaCl was added to the reaction mixture to a final concentration of about 5M (saturation) and the high salt mixture was loaded onto a phenyl Sepharose (Pharmacia Fast Flow High Substitution) column. Approximately 1 ml of phenyl Sepharose was appropriate for 10 mg protein loaded. CSF-1 was eluted from the column with an ammonium sulfate gradient from 1.2–0M in 0.1M Tris, pH 8.5. Fractions were analyzed by Coomassie-stained non-reducing SDS-PAGE and bioactivity in the NFS 60 bioassay was determined. The results are shown in Table III. The pulses show relative amounts of different CSF-1 conjugates in the samples. The bioactivity data is the average of three assays.

TABLE III

Bioactivities of PEG-CSF-1 Conjugates

| Fraction | CSF-1 Conjugates Present #PEGs/CSF-1 | | | | Bioactivity (U/mg) |
|---|---|---|---|---|---|
| | 0 | 1 | 2 | 3 | |
| 1 | + + + + | | | | $1.4 \times 10^8$ |
| 2 | + + + | + + | | | $1.4 \times 10^8$ |
| 3 | + + | + + + | | | $8.1 \times 10^7$ |
| 4 | + | + + + | | | $5.7 \times 10^7$ |
| 5 | + | + + + + | | | $6.1 \times 10^7$ |
| 6 | | + + + + | + | | $7.3 \times 10^7$ |
| 7 | | + + + | + | + | $8.3 \times 10^7$ |
| 8 | | + + | + + | + | $9.3 \times 10^7$ |
| 9 | | + | + + | + + | $6.4 \times 10^7$ |

TABLE IV

| Sample | $A_{280}$ Units | Yield(%) | Endotoxin (LAL as described above) (ng/mg protein) |
|---|---|---|---|
| Unmodified rCSF-1 | 40.0 | 100 | 0.14 |
| Pool 1, SEC | 12.2 | 30 | ND* |
| Pool 2, SEC | 6.2 | 15 | 0.43 |

*Not done

TABLE V

| Sample | RIA (as described above) ("units"/$A_{280}$ unit) | Bioassay (using a CSF-1 dependent cell line) (units/$A_{280}$ unit) | Bioassay (using a CSF-1 dependent cell line) (units/mg) |
|---|---|---|---|
| Unmodified rCSF-1 | $1 \times 10^8$ | $1 \times 10^8$ | $1.5 \times 10^8$ |
| Pool 2, SEC | $2.7 \times 10^8$ | $1.1 \times 10^8$ | $1.6 \times 10^8$ |

EXAMPLE IV

A. Preparation of PEGylated CSF-1 (SCSF/N∇3C∇158)

Growth and harvest of E. coli strain HW 22 transformed with pJN653 containing the SCSF/N∇3C∇158 gene was as described in Example I.

The refractile body suspension was then solubilized, refolded, and purified also as described in Example I. The final specific activity was about $1.5 \times 10^8$ units/mg in a CSF-1 bioassay performed on a CSF-1 dependent cell line.

At a concentration of 2.6 mg/ml in 10 mM Hepes buffer, pH 7.5 and 100 mM NaCl, 40 mg of the refolded CSF-1 above was incubated with stirring at 20° C. PEG″-11,000 was dissolved in 200 μl of distilled water and added immediately to the CSF-1 solution at an 11-fold molar excess of PEG″-11,000 over CSF-1 dimer (the PEG″-11,000 was approximately 55% non-hydrolyzed and active). After 30 minutes of incubation, the reaction was stopped by addition of 2 moles of ε-aminocaproate per mole of PEG″-11,000, from a 1M stock solution. The sample was concentrated to 6 ml by Amicon Centricon-30 centrifugation and purified by size exclusion HPLC in three identical 2-ml-load runs. The column used was Bio-Sil® TSK-250, 600×21.5 mm (BioRad), equilibrated in 0.2M $Na_2HPO_4$/$NaH_2PO_4$ buffer pH 7.0.

The $A_{280}$ peaks of mildly PEGylated protein in the three runs were pooled (pool 1, SEC) and concentrated to a final 2-ml volume, which was reinjected on the same column. The active, PEGylated fractions were pooled and concentrated.

The final pool (pool 2, SEC), representing 15% of the starting material, consisted of 6 mg of CSF-1 that had approximately 100% of the initial bioactivity of the unmodified CSF-1 and contained a major species of PEG-CSF-1 that migrated at about 45K apparent $M_r$ on SDS-PAGE. Small amounts (about 10%) of unmodified CSF-1 and more highly modified CSF-1 remained in the pooled product. Characterization of size exclusion chromatography (SEC) pools 1 and 2 is shown in Tables IV and V tables below:

B. Pharmacokinetics of PEGylated CSF-1 (SCSF/N∇3C∇158)

The same conditions as described in Example I were used to estimate the average intravenous clearance rate in three rats of CSF-1 and PEG-CSF-1 described in Section A of this example, except that the doses for both PEGylated and non-PEGylated CSF-1 were 6 mg/kg.

Figure 7:
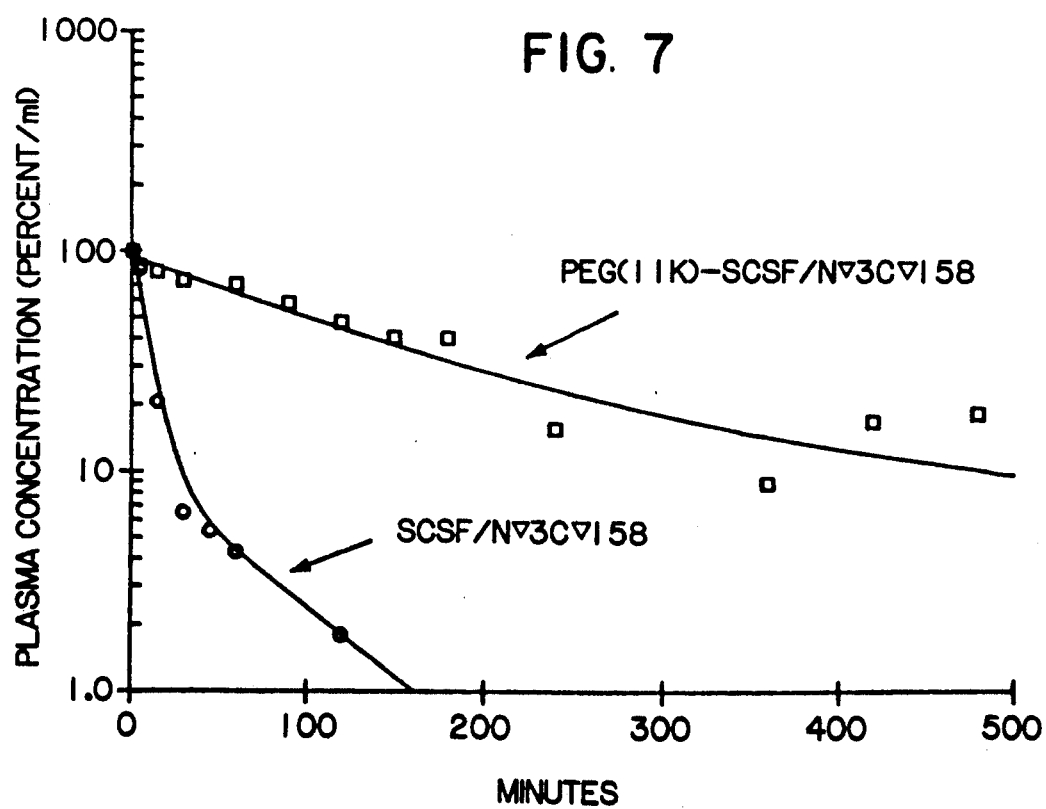
FIG. 7 shows a graph of CSF-1 concentration in rat blood plasma versus time for E. coli rCSF-1 (SCSF/N∇3C∇158) and for the same protein derivatized with 11,000 PEG.

FIG. 7 shows the curve of relative concentration of CSF-1 from the blood of three rats versus time after intravenous injection. The clearance was found to be about 0.63 ml/min/kg for PEGylated CSF-1 and 7.50 ml/min/kf for non-PEGylated CSF-1 (three hours as opposed to five minutes). This represents about a 12-fold increase in average residence time in the blood for the PEGylated molecule.

EXAMPLE V

Ammonium Sulfate Fractionation of PEG-CSF-1 Conjugates

A. Small Scale 10 ml of reaction mixture containing OPEG-CSF-1 (unconjugated CSF-1), 1 PEG-CSF-1 (1 mole PEG/mole CSF-1), 2PEG-CSF-1 (2 moles PEG/mole CSF-1), 3PEG-CSF-1 (3 moles PEG/mole CSF-1) and 4PEG-CSF-1 (4 moles PEG/mole CSF-1) was approximately 1 mg/ml protein. Solid $(NH_4)_2SO_4$ was added to about 1.3M. A precipitate formed and was removed by centrifugation at 10,000 rpm for 10 min. The pellet was saved and $(NH_4)_2SO_4$ was added to the supernatant until it became turbid at about 1.4M. The precipitate was removed by centrifugation. This procedure was continued making additional $(NH_4)_2SO_4$ cuts at about 1.5, 1.6 and 1.7M. Precipitates were resuspended in 0.1M Tris pH 8.6. SDS-PAGE analysis of the precipitates showed enrichment of unconjugated CSF-1 in the 1.7M$(NH_4)_2SO_4$ precipitate and of the 1PEG-CSF-1 species in the 1.5 and 1.6M precipitates. The 2PEG-CSF-1 was the predominant species in the 1.4M precipitates although 1PEG-and 3PEG-CSF-1 were also present. Table VI shows the relative amounts of various CSF-1 conjugates in pellets of increasing $(NH_4)_2SO_4$ concentration as analyzed by Coomassie stained non-reducing SDS-PAGE. Repeated $(NH_4)_2SO_4$ fractionation of fractions containing more than one species of CSF-1 conjugate resulted in essentially pure unconjugated CSF-1 and 1PEG-CSF-1. This repetition can also be used to produce substantially pure 2PEG-CSF-1 or 3PEG-CSF-1.

TABLE VI

Ammonium Sulfate Fractionation of PEG-CSF-1 Conjugates

| Fraction | CSF-1 Conjugate Present (#PEGs/CSF-1 Dimer) | | | | |
|---|---|---|---|---|---|
| | 0 | 1 | 2 | 3 | 4 |
| 1.3M | + | + | + | + | + |
| 1.4M | + | + | ++ | + | |
| 1.5M | + | +++ | | | |
| 1.6M | + | +++ | | | |
| 1.7M | +++++ | | | | |

B. Large Scale

Approximately 1 g of CSF-1 (SCSF/N∇3C∇158) was conjugated according to Example III. After fractionation by $(NH)_2SO_4$ as described in Part A, approximately 600 mg of CSF-1 having the molecular weight of CSF-1 dimer conjugated to one PEG was purified. This conjugate had a specific activity of about $6.2 \times 10^7$ U/mg. About 80 mg of a mixture of CSF-1 conjugates having 1, 2 or 3 PEGs linked was also recovered and had a specific activity of about $3.2 \times 10^7$ U/mg.

EXAMPLE VI

Ammonium Sulfate Fractionation of PEG-IL-2 Conjugates

A. PEG-IL-2 Conjugates having an Amide Linker

Approximately 12 mg of IL-2 which was produced and purified essentially as described in PCT Patent Publication No. WO 88/08849 published Nov. 17, 1988 and PEGylated essentially as described in U.S. Pat. No. 7,766,106 was resuspended in 1 ml 1.0M Tris pH8. Solid $(NH)_2SO_4$ was added until the solution became turbid. The sample was centrifuged at 12,000 rpm for 12 min. The pellet was resuspended in 0.1M Tris pH 8.6. $(NH)_2SO_4$ fractionation was continued as described in Example V and SDS-PAGE analysis of resuspended pellets indicated that unconjugated IL-2 could be separated from conjugated IL-2. Furthermore, similar to the results described in Example V for CSF-1, fractions were obtained that were obtained that were enriched for IL-2 conjugated to 1PEG. Recycling of fractions enriched for a particular conjugate is expected to result in substantially pure conjugate.

B. PEG-IL-2 Conjugates having the Urethane Linker

PEG-IL-2 was obtained by the procedures described in commonly owned copending U.S. Ser. No. 146,275 filed on Jan. 20, 1989. The PEG moiety was attached to IL-2 via the urethane linker herein described. $(NH)_2SO_4$ precipitation essentially as described in Example VI Part A and in Example V resulted in fractionation of the various PEG-IL-2 conjugates.

EXAMPLE VII

In vivo Efficacy of PEGylated CSF-1 (SCSF/N∇3C∇158): bacterial infection model

Groups of five mice were injected intraperitoneally (ip) on day-1 (a day prior to infection with a lethal dose of *E. coli* SM18) with the SCSF/N∇3C∇158 described in Example III, PEGylated SCSF/N∇3C∇158 prepared as described in Example III, or saline (control group). Two CSF-1 dosage groups (10 μg/mouse and 50 μg/mouse) were used. At day 0, all mice were injected ip with a lethal dose ($5 \times 10^7$ cells) of *E. coli* SM18. The number of mice surviving was followed for five days. The results are shown in the table below:

TABLE VII

| | Number of Mice Surviving after day: | | | | | |
|---|---|---|---|---|---|---|
| | 1 | 2 | 3 | 4 | 5 | 6 |
| Control (saline injected) | 2 | 0 | 0 | 0 | 0 | 0 |
| Unmodified CSF-1 | | | | | | |
| 10 μg | 3 | 2 | 2 | 2 | 2 | 2 |
| 50 μg | 3 | 3 | 3 | 3 | 3 | 3 |
| PEGylated CSF-1 | | | | | | |
| 10 μg | 2 | 2 | 1 | 1 | 1 | 1 |
| 50 μg | 5 | 4 | 3 | 3 | 3 | 3 |

The results show that there is a dose-dependent effect of rCSF-1 on survival. The slight difference between the modified and unmodified CSF-1 in efficacy in this single experiment is not statistically significant. PEGylation of CSF-1 did not reduce the efficacy detected by this protocol, nor did it increase drug-related toxicity observable in this experiment.

EXAMPLE VIII

In Vivo Test of Conjugated CSF-1 for Anti-Tumor Efficacy

A. Meth A Sarcoma Model

PEGylated CSF-1 is injected intraperitoneally, subcutaneously or intravenously (i.p., s.c., i.v.) at up to 50 μg/dose per mouse (10 mice per group) implanted subcutaneously with a Meth A sarcoma tumor 7 days earlier. Dosing schedules depend upon the particular PEGylated CSF-1 preparation used. Tumor volume is followed for 14 days after the beginning of CSF-1 treatment. The results are evaluated by comparing the mean change in tumor volume* over time in the CSF-1 treated and control treated mice. *($\Delta TV$ = Ratio of the mean tumor volume at the day indicated to the mean tumor volume at day 0 within a single group of mice).

B. B16 Metastases Model

A second in vivo tumor model using PEGylated CSF-1 to prevent metastases in the B16 murine melanoma cell line is also useful.

$1-10 \times 10^4$ tumor cells, suspended in 0.2 ml of $Ca^{+2}$ and $Mg^{+2}-$ free HBSS, are inoculated into unanesthetized mice in the lateral tail vein. From 14 to 21 days after tumor cell inoculation, the mice are sacrificed and necropsied. During necropsy, the lungs and brain are removed, rinsed in water, and weighed. The lungs are then fixed in Bouin's solution, and the number of surface tumor nodules per pair of lungs are determined with the aid of a dissecting microscope.

Recombinant human CSF-1 PEGylated prepared according to Example III and having a potency of $1-25 \times 10^7$ U/mg and pharmacologically acceptable endotoxin levels is used. CSF-1 is freshly obtained prior to each experiment from frozen stocks and diluted immediately prior to injection in USP 0.9% saline. PEGylated CSF-1 is delivered i.v., i.p. or s.c. on schedules which are dependent upon the particular PEGylated CSF-1 CSF-1 preparation used. The dosing levels used ranged up to 5 mg/kg. As a negative control consisting of a non-specific and non-therapeutic protein, either USP human serum albumin (HSA) or boiled PEGylated CSF-1 is used. PEGylated CSF-1 is boiled for 30 min to inactivate the CSF-1 activity.

The efficacy data demonstrates that PEGylated CSF-1 produces a significant reduction in the median number of pulmonary metastases.

EXAMPLE IX

In Vivo Treatment of CMV Infection with PEGylated CSF-1

Outbred CD-1 mice are treated i.p., i.v. or s.c. with PEGylated CSF-1 at doses of up to 400 µg/kg, starting two days before infection with a sub-lethal dose of cytomegalovirus (CMV). Dosing schedules are dependent upon the particular PEGylated CSF-1 preparation used. Mice are sacrificed on the third day after infection and the extent of viral replication in target organs such as the spleen is evaluated by plaque assay. The results show that mice treated with PEGylated CSF-1 have significantly lowered organ viral titer compared to the saline-treated control mice, indicating that CMV infection is less severe in PEGylated CSF-1 treated mice.

Separately, PEGylated CSF-1 may be tested in a lethal murine CMV infection model in outbred CD-1 mice (this is in contrast to the above experiment using sub-lethal doses of CMV, in which organ titers are monitored). When PEGylated CSF-1 is administered i.p., s.c. or i.v. to mice at doses up to 4 mg/kg (per mouse) starting up to 24 hours before viral challenge, there is a significant increase in survival as compared to saline-treated control.

Thus, PEGylated CSF-1 may be used alone or in combination with another lymphokine in the treatment of viral infections in general, and in particular, may be beneficial in immunosuppressive viral infection such as acquired immune deficiency syndrome (AIDS).

EXAMPLE X

In Vivo Stimulation of White Blood Cell Count

Outbred CD-1 mice are administered purified recombinant human CSF-1 PEGylated as described in Example III, in amounts up to approximately 2 mg/kg per dose on various dosing schedules which are dependent upon the PEGylated CSF-1 preparation used. Total white blood cell count, neutrophil count, monocyte count and lymphocyte counts are determined. Increases in any of these parameters may be useful in clinical or veterinary medicine as a stimulus of granulocyte or monocyte production and an enhancer of white blood count.

EXAMPLE XI

PEGylated CSF-1 in Wound Healing

PEGylated CSF-1 is assayed for wound healing using animal models and protocols such as the Goretex miniature wound healing model of Goodson and Hunt, 1982, *J. Surg. Res.*, 33:394, in which implanted Goretex tubes fill up with invading macrophages, fibroblasts and other connective tissue cells, and collagen and fibrin deposition. Healing is assessed by examining tube contents microscopically. A second model is the incisional wound healing model of Eisenger, et al., 1988, *Proc. Natl. Acad. Sci., USA*, 85:1937, in which wounds are observed visually and punch biopsies are taken to monitor healing, density of cells, and number of epidermal cell layers arising from hair follicles. Also at the end of the experiment wound breaking strength is determined. A third model is a serosal model such as the heat-injured testicular serosa of Fotev, et al., 1987, *J. Pathol.*, 151:209, in which healing is assessed in fixed sections by degree of mesothelial resurfacing of the injured site. The teachings of each of these models are incorporated herein by reference.

Generally, PEGylated CSF-1 is applied to the site of the wound by soaking a nonadhesive surgical dressing in amounts up to 1,000,000 U/ml of PEGylated CSF-1 in saline under sterile conditions as described in the incisional wound healing model reference using epidermal cell derived factor (EDF) for topical wounds. Alternatively, similar amounts of PEGylated CSF-1 are introduced into Goretex tubes at the time of implantation as described in Goodson and Hunt, ibid, or PEGylated CSF-1 may also be incorporated into a slow-release matrix and applied at the site of the wound (in Goretex tubes, in or under dressings, or by injection in the serosal cavity) or PEGylated CSF-1 is administered systemically (i.v., i.p., or s.c.) at doses of up to 1,000 µg/kg/day.

The healing rate of each model is measured and tissure repair evaluated in the presence and in the absence of PEGylated CSF-1.

PEGylated CSF-1 may also be used in combination with other growth factors to promote wound healing such as EDF, epidermal growth factor (EGF), fibroblast growth factor (basic and acidic FGF), platelet derived growth factor (PDGF), or transforming growth factors (TGF alpha and beta), IL-1 and other substances such as somatomedin C and vitamin C.

EXAMPLE XII

Preparation of PEGylated LCSF

A. Conjugation

PEG"-11,000 was prepared as described in Example IA. CSF-1 (LCSF/N∇3C∇221) was prepared according to fermentation purification and refolding procedures disclosed in PCT Publication No. WO88/08003 published Oct. 20, 1988. 5 mg of LCSF was dialyzed into 20 mM HEPES buffer, pH 7.5, containing 50 mM NaCl. PEG"-11,000 was added at 6-fold molar excess over LCSF dimer. The dry activated PEG was added to the stirring 2 mg/ml LCSF solution at 20° C. Aliquots of the reaction mixture were analyzed every 10 min by size exclusion HPLC (SEC) on Zorbax GF250 (Dupont). The reaction was stopped by addition of a 10-fold excess of ε-aminocaproate over PEG. Table VIII shows NFS 60 bioassay data of the PEG-LCSF reaction mixtures.

Samples containing 2 mg/ml of M-CSF were diluted into PBS containing 12 mg/ml BSA and assayed in the NFS 60 assay. Values represent the mean of duplicate determination performed on serial dilutions of each sample.

TABLE VIII

| NFS Bioassay of PEG-LCSF/N∇3C∇221 | |
|---|---|
| Sample | U/ml CSF-1 Activity |
| starting material | $3.65 \times 10^7$ |
| 10 min + PEG | $2.51 \times 10^7$ |
| 20 min + PEG | $3.30 \times 10^7$ |
| 30 min + PEG | $1.68 \times 10^7$ |

Size exclusion analysis of the PEGylation reaction showed two major species of PEG-CSF after the 30 min reaction. Their sizes were consistent with an approximate derivatization of 1 and 2 moles PEG per mole CSF-1 dimer. The SEC profile after 45 min indicated that the reaction had reached completion at about 30 min.

B. Separation of PEG-LCSF from Unmodified LCSF

The sample was adjusted to pH 8.3 with 1M Tris-HCl, diafiltered to educe salt concentration to 30 mM and applied to a Bio-Gel ® TSK-DEAE-5-PW HPLC 75×7.5 mm column. The column was equilibrated in 30 mM Tris-HCl, pH 8.5, and was developed with a 40 min gradient of 0 to 0.6M NaCl. All buffers were prepared with depyrogenated water, and the HPLC system was prewashed with 0.1M NaOH and with 50% ethanol to remove endotoxin. Fractions off the column were analyzed by SDS-PAGE. PEGylated species eluted earlier than unmodified CSF-1 from the column. Some PEG-CSF also appeared in the column passthrough and this material again did not bind upon reapplication to the column. The unbound fraction also contained released NHS anion.

Other Embodiments

The reaction herein may also be carried out employing polyvinyl alcohol or a polyoxyethylated polyol. An active POG-CSF-1 may be prepared as follows.

Polyoxyethylated glycerol (POG) of molecular weight 5000 may be obtained from Polysciences. To 10 g of POG may be added 2.28 g glutaric anhydride (a 10-fold excess over POG). The mixture may be stirred for two hours at 110° C. and cooled. This may be dissolved in 20 ml CHCl$_3$ and poured slowly into 500 ml ether with vigorous stirring. The product may be collected and rinsed with ether to yield about 90% POG-glutarate product. This product may be reacted with N-hydroxysuccinimide as described in Example IA to yield the active ester POG-glutaryl N-hydroxysuccinimide (POG*). Then one of the CSF-1 proteins described above may be reacted with the POG*.

Nitrile-substituted polyvinyl alcohol may also be used to prepare an activated polyvinyl alcohol for conjugation to the CSF-1.

Deposits

The following cultures described more fully in PCT Publication No. WO 86/04607 and in European Patent Publication No. 0272779, were deposited in the Cetus Master Culture Collection (CMCC), 1400 Fifty-Third Street, Emeryville, CA 94608 USA and in the American Type Culture Collection (ATCC), 12301 Parklawn Drive, Rockville, Md. 20852 USA. The CMCC and ATCC accession numbers and ATCC deposit dates for the deposited samples are:

| Culture Designation | CMCC No. | ATCC No. | ATCC Deposit Date |
| --- | --- | --- | --- |
| Phage pH CSF-1 in E. coli DG98 | | 40,177 | April 2, 1985 |
| pHCSF-1 λ Charon 4A | 2312 | 40,185 | May 21, 1985 |
| CSF-17 in E. coli MM294 | 2347 | 53,149 | June 14, 1985 |
| pCSF-asp$_{59}$ | 2705 | 67,139 | June 19, 1985 |
| pCSF-gln$_{52}$ | 2708 | 67,140 | June 19, 1986 |
| pCSF-pro$_{52}$ | 2709 | 67,141 | June 19, 1985 |
| pCSF-Bam | 2710 | 67,142 | June 19, 1986 |
| pCSF-BamBcl | 2712 | 67,144 | June 19, 1986 |
| pCSF-Gly150 | 2762 | 67,145 | June 19, 1986 |
| pcDBCSF4 (or pcDBhuCSF-4) | 2894 | 67,250 | October 24, 1986 |
| pPho-A-LCSF/C∇221 in MM294 | 3084 | 67,391 | April 14, 1987 |
| O/E pP$_L$LCSF/N∇3C∇221 in DG116 | 3095 | 67,390 | April 14, 1987 |
| O/E pP$_L$CSF-17 asp$_{59}$/C∇150 | 3044 | 67,389 | April 14, 1987 |
| in DG116 pP$_L$CSF-17asp$_{59}$/C∇150 in DG116 | 2946 | 67,383 | April 7, 1987 |
| pJN653 (SCSF/N∇3C∇158) in HW22 | 3204 | 67,561 | November 12, 1987 |

The deposits above were made pursuant to a contract between the ATCC and the assignee of this patent application, Cetus Corporation. The contract with ATCC provides for permanent availability of the progeny of these plasmids and the cell line to the public on the issuance of the U.S. patent describing and identifying the deposit or the publications or upon the laying open to the public of any U.S. or foreign patent application, whichever comes first, and for availability of the progeny of these plasmids and the cell line to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the plasmids and the cell line on deposit should die or be lost or destroyed when cultivated under suitable conditions, they will be promptly replaced on notification with a viable culture of the same plasmids and cell line.

In summary, the present invention is seen to provide various recombinant CSF-1 molecules selectively derivatized with water-soluble polymers of different sizes using different chemical linkers. Derivatization of the CSF-1 increases the apparent molecular weight of the CSF-1 and increases its in vivo half-life in the plasma of rats. The derivatization may also increase the solubility of the CSF-1 in aqueous medium at physiological pH and may decrease its immunogenicity by decreasing or eliminating aggregation or by shielding its antigenic determinants.

The foregoing written specification is considered to be sufficient to enable one skilled in the art to practice the invention. The present invention is not to be limited in scope by the cultures deposited, since the deposited embodiments are intended as a single illustration of one aspect of the invention, and any cultures that are functionally equivalent are within the scope of this invention. The deposit of materials herein does not constitute an admission that the written description herein contained is inadequate to enable the practice of any aspect of the invention, including the best mode thereof, nor are they to be construed as limiting the scope of the claims to the specific illustrations that they represent. Indeed, various modifications of the above-described modes for carrying out the invention that are obvious to those skilled in the field of pharmaceutical formulation or related fields are intended to be within the scope of the following claims.

We claim:

1. A biologically active composition comprising a protein that stimulates the formation of primarily macrophage colonies in the in vitro colony stimulating factor-1 (CSF-1) assay, which protein is covalently conjugated to a water-soluble polymer selected from the group consisting of polyethylene or polypropylene glycol homopolymers, polyoxyethylated polyols, and polyvinyl alcohol, wherein said homopolymer is unsubstituted or substituted at one end with an alkyl group, the invention comprises a polymer/CSF-1 conjugate that is linked by a urethane bond between the polymer and at least one free amino group on CSF-1, the conjugate has the chemical formula:

$$\text{Polymer}-\text{O}-\overset{\overset{\text{O}}{\|}}{\text{C}}-\text{NH}-\text{CSF-1}$$

2. The composition of claim 1 wherein the protein is a native human CSF-1.

3. The composition of claim 1 wherein the protein is a recombinant human CSF-1.

4. The composition of claim 3 wherein the protein is recombinantly expressed in bacteria and is a homodimer with predicted amino acid sequence selected from the group consisting of LCSF/C∇150 through C∇464; tyr$_{59}$LCSF/C∇150 through C∇464; SCSF/C∇150 through C∇166; asp$_{59}$SCSF/C∇150 through C∇166; and the gln$_{52}$ muteins and N∇2 and N∇3 muteins thereof, wherein LCSF is coded for by the sequence shown as amino acids 1–522 of FIG. 2 as shown below:

Leu Leu Leu Leu Val Cys Leu Leu Ala Ser Arg Ser Ile Thr

Glu Glu Val Ser Glu Tyr Cys Ser His MET Ile Gly Ser Gly His Leu Gln Ser Leu Gln

Arg Leu Ile Asp Ser Gln MET Glu Thr Ser Cys Gln Ile Thr Phe Glu Phe Val Asp Gln

Glu Gln Leu Lys Asp Pro Val Cys Tyr Leu Lys Lys Ala Phe Leu Leu Val Gln Asp Ile

MET Glu Asp Thr MET Arg Phe Arg Asp Asn Thr Pro Asn Ala Ile Ala Ile Val Gln Leu

Gln Glu Leu Ser Leu Arg Leu Lys Ser Cys Phe Thr Lys Asp Tyr Glu Glu His Asp Lys

Ala Cys Val Arg Thr Phe Tyr Glu Thr Pro Leu Gln Leu Leu Glu Lys Val Lys Asn Val

Phe Asn Glu Thr Lys Asn Leu Leu Asp Lys Asp Trp Asn Ile Phe Ser Lys Asn Cys Asn

Asn Ser Phe Ala Glu Cys Ser Ser Gln Asp Val Val Thr Lys Pro Asp Cys Asn Cys Leu

Tyr Pro Lys Ala Ile Pro Ser Ser Asp Pro Ala Ser Val Ser Pro His Gln Pro Leu Ala

Pro Ser MET Ala Pro Val Ala Gly Leu Thr Trp Glu Asp Ser Glu Gly Thr Glu Gly Ser

Ser Leu Leu Pro Gly Glu Gln Pro Leu His Thr Val Asp Pro Gly Ser Ala Lys Gln Arg

Pro Pro Arg Ser Thr Cys Gln Ser Phe Glu Pro Pro Glu Thr Pro Val Val Lys Asp Ser

Thr Ile Gly Gly Ser Pro Gln Pro Arg Pro Ser Val Gly Ala Phe Asn Pro Gly MET Glu

Asp Ile Leu Asp Ser Ala MET Gly Thr Asn Trp Val Pro Glu Glu Ala Ser Gly Glu Ala

Ser Glu Ile Pro Val Pro Gln Gly Thr Glu Leu Ser Pro Ser Arg Pro Gly Gly Gly Ser

MET Gln Thr Glu Pro Ala Arg Pro Ser Asn Phe Leu Ser Ala Ser Ser Pro Leu Pro Ala

Ser Ala Lys Gly Gln Gln Pro Ala Asp Val Thr Gly Thr Ala Leu Pro Arg Val Gly Pro

Val Arg Pro Thr Gly Gln Asp Trp Asn His Thr Pro Gln Lys Thr Asp His Pro Ser Ala

Leu Leu Arg Asp Pro Pro Glu Pro Gly Ser Pro Arg Ile Ser Ser Leu Arg Pro Gln Gly

Leu Ser Asn Pro Ser Thr Leu Ser Ala Gln Pro Gln Leu Ser Arg Ser His Ser Ser Gly

Ser Val Leu Pro Leu Gly Glu Leu Glu Gly Arg Arg Ser Thr Arg Asp Arg Arg Ser Pro

Ala Glu Pro Glu Gly Gly Pro Ala Ser Glu Gly Ala Ala Arg Pro Leu Pro Arg Phe Asn

Ser Val Pro Leu Thr Asp Thr Gly His Glu Arg Gln Ser Glu Gly Ser Ser Ser Pro Gln

Leu Gln Glu Ser Val Phe His Leu Leu Val Pro Ser Val Ile Leu Val Leu Leu Ala Val

Gly Gly Leu Leu Phe Tyr Arg Trp Arg Arg Arg Ser His Gln Glu Pro Gln Arg Ala Asp

Ser Pro Leu Glu Gln Pro Glu Gly Ser Pro Leu Thr Gln Asp Asp Arg Gln Val Glu Leu

Pro Val and SCSF is coded for by the sequence shown as amino acids 1–224 of FIG. 1 as shown below:

Glu Glu

Val Ser Glu Tyr Cys Ser His Met Ile Gly Ser Gly His Leu Gln Ser

Leu Gln Arg Leu Ile Asp Ser Gln Met Glu Thr Ser Cys Gln Ile Thr Phe Glu

Phe Val Asp Gln Glu Gln Leu Lys Asp Pro Val Cys Tyr Leu Lys

-continued

Lys Ala Phe Leu Leu Val Gln Tyr Ile Met Glu Asp Thr Met Arg Phe Arg Asp

Asn Thr Pro Asn Ala Ile Ala Ile Val Gln Leu Gln Glu Leu Ser

Leu Arg Leu Lys Ser Cys Phe Thr Lys Asp Tyr Glu Glu His Asp Lys Ala

Cys Val Arg Thr Phe Tyr Glu Thr Pro Leu Gln Leu Leu Glu Lys Val

Lys Asn Val Phe Asn Glu Thr Lys Asn Leu Leu Asp Lys Asp Trp Asn Ile

Phe Ser Lys Asn Cys Asn Asn Ser Phe Ala Glu Cys Ser Ser Gln Gly

His Glu Arg Gln Ser Glu Gly Ser Ser Ser Pro Gln Leu Gln Glu Ser Val

Phe His Leu Leu Val Pro Ser Val Ile Leu Val Leu Leu Ala Val Gly

Gly Leu Leu Phe Tyr Arg Trp Arg Arg Arg Ser His Gln Glu Pro Gln Arg

Ala Asp Ser Pro Leu Glu Gln Pro Glu Gly Ser Pro Leu Thr Gln Asp

Asp Arg Gln Val Glu Leu Pro Val.

5. The composition of claim 4 wherein the protein is a homodimer with predicted amino acid sequence selected from the group consisting of LCSF/C∇150; tyr$_{59}$LCSF/C∇150; LCSF/C∇190; tyr$_{59}$LCSF/C∇190; LCSF/C∇191; tyr$_{59}$LCSF/C∇191; LCSF/C∇221; tyr$_{59}$LCSF/C∇221; LCSF/C∇223; tyr$_{59}$LCSF/C∇223; LCSF/C∇236; tyr$_{59}$LCSF/C∇236; LCSF/C∇238; tyr$_{59}$LCSF/C∇238; LCSF/C∇249; tyr$_{59}$LCSF/C∇249; LCSF/C∇258; tyr$_{59}$LCSF/C∇258; LCSF/C∇411; tyr$_{59}$LCSF/C∇411; LCSF/C∇464; tyr$_{59}$LCSF/C∇464; SCSF/C∇150; SCSF/C∇153; SCSF/C∇158; the corresponding asp$_{59}$SCSFs; and the gln$_{52}$ muteins and N∇2 and N∇3 muteins thereof.

6. The composition of claim 5 wherein the protein is a homodimer coded for by a sequence selected from the group consisting of LCSF/C∇150, LCSF/C∇190, LCSF/C∇221, tyr$_{59}$LCSF/C∇150, tyr$_{59}$LCSF/C∇190, tyr$_{59}$LCSF/C∇221, SCSF/C∇158, SCSF/C∇150, asp$_{59}$SCSF/C∇158; asp$_{59}$SCSF/C∇150; and the N∇2 and N∇3 muteins thereof.

7. The composition of claim 6 wherein the protein is a homodimer coded for by a sequence selected from the group consisting of SCSF/C∇150, asp$_{59}$SCSF/C∇150, SCSF/N∇3C∇150, asp$_{59}$SCSF/N∇3C∇150, SCSF/N∇3C∇158, asp$_{59}$SCSF/N∇3C∇158 asp$_{59}$SCSF/N∇2C∇150 and asp$_{59}$SCSF/N∇2C∇158.

8. The composition of claim 1 wherein the protein is a recombinant heterodimer consisting of one subunit containing a cysteine residue with a free sulfhydryl group reactive with the polymer.

9. The composition of claim 1 wherein the protein is a murine CSF-1.

10. The composition of claim 1 wherein the protein is a human CSF-1 expressed in and secreted from a eukaryotic host.

11. The composition of claim 10 wherein the protein is a dimer coded for by a sequence selected from the group consisting of LCSF/C∇150; tyr$_{59}$LCSF/C∇150; LCSF/C∇190; tyr$_{59}$LCSF/C∇190; LCSF/C∇191; tyr$_{59}$LCSF/C∇191; LCSF/C∇221; tyr$_{59}$LCSF/C∇221; LCSF/C∇223; tyr$_{59}$LCSF/C∇223; LCSF/C∇236; tyr$_{59}$LCSF/C∇236; LCSF/C∇238; tyr$_{59}$LCSF/C∇238; LCSF/C∇249; tyr$_{59}$LCSF/C∇249; LCSF/C∇258; tyr$_{59}$LCSF/C∇258; LCSF/C∇411; tyr$_{59}$LCSF/C∇411; LCSF/C∇464; tyr$_{59}$LCSF/C∇464; SCSF/C∇150; SCSF/C∇153; SCSF/C∇158; the corresponding asp$_{59}$SCSFs; and the gln$_{52}$ muteins thereof.

12. The composition of claim 10 wherein the eukaryotic host is mammalian, insect, yeast, or fungal cells.

13. The composition of claim 1 wherein said polymer has an average molecular weight of about 1000 to 100,000 daltons.

14. The composition of claim 1 wherein said polymer has an average molecular weight of 4000 to 40,000 daltons.

15. The composition of claim 1 wherein said polymer is an unsubstituted polyethylene glycol homopolymer, a monomethyl polyethylene glycol homopolymer or a polyoxyethylated glycerol.

16. The composition of claim 1 wherein the amino group(s) conjugated is (are) in lysine residue(s) or the N-terminal amino acid or a combination thereof.

17. A pharmaceutical preparation comprising the composition of claim 1 dissolved in a pharmaceutically acceptable aqueous carrier medium.

18. The preparation of claim 17 wherein the protein is refolded, and purified in vitro and is the product of a recombinant CSF-1 clone recombinantly expressed in bacteria.

19. The preparation of claim 18 wherein the protein is a biologically active, refolded CSF-1 dimer having an endotoxin content of less than 1.0 ng/mg of CSF-1 and substantially free of pyrogens.

20. The composition of claim 1 wherein there are between 1 and 3 moles polymer, inclusive, per mole CSF-1 dimer.

21. The composition of claim 1 wherein said covalently conjugated protein is substantially pure with respect to the number of moles polymer per mole CSF-1.

22. The composition of claim 21 wherein said substantially pure conjugated protein is obtained by ammonium sulfate fractionation.

23. A process for preparing a conjugated protein, which protein stimulates the formation of primarily macrophage colonies in the in vitro colony stimulating factor-1 (CSF-1) assay, comprising:
(a) contacting a water-soluble polymer having at least one terminal reactive group with a chloroformate under the appropriate reaction conditions to form a polymer active ester, where said polymer is selected from the group consisting of polyethylene or polypropylene glycol homopolymers, polyoxyethylated polyols, and polyvinyl alcohol, wherein said homopolymer is unsubstituted or substituted at one end with an alkyl group;

(b) contacting the polymer active ester with CSF-1 under the appropriate reaction conditions to form a polymer CSF-1 conjugate that is linked with a urethane bond; and (c) purifying the conjugated protein.

24. The process of claim 23 wherein said polymer has an average molecular weight of about 1000 to 100,000 daltons.

25. The process of claim 23 wherein said polymer is an unsubstitued polyethylene glycol homopolymer, a monomethyl polyethylene glycol homopolymer, or a polyoxyethylated glycerol.

26. The process of claim 23 wherein the protein is a recombinant human CSF-1.

27. The process of claim 23 wherein the protein is a human CSF-1 expressed in and secreted from a eukaryotic host.

28. The process of claim 23 further comprising, after step (c), the step of formulating the protein in a pharmaceutically acceptable aqueous carrier medium.

29. The process of claim 23 wherein the protein is glycosylated and is conjugated to the polymer via at least one of the carbohydrate moieties on the protein, and the polymer contains an amino, hydrazine, or hydrazide group that reacts with free aldehydes formed by oxidation of the carbohydrate moieties.

30. The process of claim 29 wherein the protein is a dimeric product of a recombinant CSF-1 clone recombinantly expressed in a eukaryotic host.

31. The process of claim 30 wherein the eukaryotic host is mammalian, yeast, insect, or fungal cells.

32. The process of claim 23 wherein step (c) comprises ammonium sulfate fractionation.

33. The process of claim 31, wherein the protein is recombinantly expressed in bacteria and is a homodimer with predicted amino acid sequence selected from the group consisting of LCSF/C∇150 through C∇464; tyr$_{59}$LCSF/C∇150 through C∇464; SCSF/C∇150 through C∇166; asp$_{59}$SCSF/C∇150 through C∇166; and the gln$_{52}$ muteins and N∇2 and N∇3 muteins thereof, wherein LCSF is coded for by the sequence shown as amino acids 1-522 of FIG. 2 as shown below:

```
                                    Leu Leu Leu Leu Val Cys Leu Leu Ala Ser Arg Ser Ile Thr

Glu Glu Val Ser Glu Tyr Cys Ser His MET Ile Gly Ser Gly His Leu Gln Ser Leu Gln

Arg Leu Ile Asp Ser Gln MET Glu Thr Ser Cys Gln Ile Thr Phe Glu Phe Val Asp Gln

Glu Gln Leu Lys Asp Pro Val Cys Tyr Leu Lys Lys Ala Phe Leu Leu Val Gln Asp Ile

MET Glu Asp Thr MET Arg Phe Arg Asp Asn Thr Pro Asn Ala Ile Ala Ile Val Gln Leu

Gln Glu Leu Ser Leu Arg Leu Lys Ser Cys Phe Thr Lys Asp Tyr Glu Glu His Asp Lys

Ala Cys Val Arg Thr Phe Tyr Glu Thr Pro Leu Gln Leu Leu Glu Lys Val Lys Asn Val

Phe Asn Glu Thr Lys Asn Leu Leu Asp Lys Asp Trp Asn Ile Phe Ser Lys Asn Cys Asn

Asn Ser Phe Ala Glu Cys Ser Ser Gln Asp Val Val Thr Lys Pro Asp Cys Asn Cys Leu

Tyr Pro Lys Ala Ile Pro Ser Ser Asp Pro Ala Ser Val Ser Pro His Gln Pro Leu Ala

Pro Ser MET Ala Pro Val Ala Gly Leu Thr Trp Glu Asp Ser Glu Gly Thr Glu Gly Ser

Ser Leu Leu Pro Gly Glu Gln Pro Leu His Thr Val Asp Pro Gly Ser Ala Lys Gln Arg

Pro Pro Arg Ser Thr Cys Gln Ser Phe Glu Pro Pro Glu Thr Pro Val Val Lys Asp Ser

Thr Ile Gly Gly Ser Pro Gln Pro Arg Pro Ser Val Gly Ala Phe Asn Pro Gly MET Glu

Asp Ile Leu Asp Ser Ala MET Gly Thr Asn Trp Val Pro Glu Glu Ala Ser Gly Glu Ala

Ser Glu Ile Pro Val Pro Gln Gly Thr Glu Leu Ser Pro Ser Arg Pro Gly Gly Gly Ser

MET Gln Thr Glu Pro Ala Arg Pro Ser Asn Phe Leu Ser Ala Ser Ser Pro Leu Pro Ala

Ser Ala Lys Gly Gln Gln Pro Ala Asp Val Thr Gly Thr Ala Leu Pro Arg Val Gly Pro

Val Arg Pro Thr Gly Gln Asp Trp Asn His Thr Pro Gln Lys Thr Asp His Pro Ser Ala

Leu Leu Arg Asp Pro Pro Glu Pro Gly Ser Pro Arg Ile Ser Ser Leu Arg Pro Gln Gly

Leu Ser Asn Pro Ser Thr Leu Ser Ala Gln Pro Gln Leu Ser Arg Ser His Ser Ser Gly

Ser Val Leu Pro Leu Gly Glu Leu Glu Gly Arg Arg Ser Thr Arg Asp Arg Arg Ser Pro

Ala Glu Pro Glu Gly Gly Pro Ala Ser Glu Gly Ala Ala Arg Pro Leu Pro Arg Phe Asn

Ser Val Pro Leu Thr Asp Thr Gly His Glu Arg Gln Ser Glu Gly Ser Ser Ser Pro Gln

Leu Gln Glu Ser Val Phe His Leu Leu Val Pro Ser Val Ile Leu Val Leu Leu Ala Val
```

-continued

Gly Gly Leu Leu Phe Tyr Arg Trp Arg Arg Arg Ser His Gln Glu Pro Gln Arg Ala Asp
Ser Pro Leu Glu Gln Pro Glu Gly Ser Pro Leu Thr Gln Asp Asp Arg Gln Val Glu Leu
Pro Val and SCSF is coded for by the sequence shown as amino acids 1-224 of FIG. 1 as shown below:

Glu Glu
Val Ser Glu Tyr Cys Ser His Met Ile Gly Ser Gly His Leu Gln Ser
Leu Gln Arg Leu Ile Asp Ser Gln Met Glu Thr Ser Cys Gln Ile Thr Phe Glu
Phe Val Asp Gln Glu Gln Leu Lys Asp Pro Val Cys Tyr Leu Lys
Lys Ala Phe Leu Leu Val Gln Tyr Ile Met Glu Asp Thr Met Arg Phe Arg Asp
Asn Thr Pro Asn Ala Ile Ala Ile Val Gln Leu Gln Glu Leu Ser
Leu Arg Leu Lys Ser Cys Phe Thr Lys Asp Tyr Glu Glu His Asp Lys Ala
Cys Val Arg Thr Phe Tyr Glu Thr Pro Leu Gln Leu Leu Glu Lys Val
Lys Asn Val Phe Asn Glu Thr Lys Asn Leu Leu Asp Lys Asp Trp Asn Ile
Phe Ser Lys Asn Cys Asn Asn Ser Phe Ala Glu Cys Ser Ser Gln Gly
His Glu Arg Gln Ser Glu Gly Ser Ser Ser Pro Gln Leu Gln Glu Ser Val
Phe His Leu Leu Val Pro Ser Val Ile Leu Val Leu Leu Ala Val Gly
Gly Leu Leu Phe Tyr Arg Trp Arg Arg Arg Ser His Gln Glu Pro Gln Arg
Ala Asp Ser Pro Leu Glu Gln Pro Glu Gly Ser Pro Leu Thr Gln Asp
Asp Arg Gln Val Glu Leu Pro Val.

* * * * *